(12) United States Patent
Ohta et al.

(10) Patent No.: US 6,626,857 B1
(45) Date of Patent: Sep. 30, 2003

(54) EXTRACORPOREAL CIRCULATION DEVICE AND METHOD FOR ISOLATION TEMPERATURE CONTROL METHOD

(75) Inventors: Tomio Ohta, 22-31, Tezukayama 1-chome, Abeno-ku, Osaka-shi, Osaka 545-0037 (JP); Tetsuya Miyatake, Shizuoka (JP); Yoshihiko Kinoshita, Tokyo (JP); Tomoya Murakami, Sapporo (JP)

(73) Assignees: Tomio Ohta, Osaka (JP); Nikkiso Co., Ltd., Tokyo (JP)

( * ) Notice: Subject to any disclaimer, the term of this patent is extended or adjusted under 35 U.S.C. 154(b) by 0 days.

(21) Appl. No.: 09/856,135

(22) PCT Filed: Nov. 18, 1999

(86) PCT No.: PCT/JP99/06434

§ 371 (c)(1),
(2), (4) Date: Jul. 23, 2001

(87) PCT Pub. No.: WO00/30702

PCT Pub. Date: Jun. 2, 2000

(30) Foreign Application Priority Data

Nov. 19, 1998 (JP) ............................................ 10-329596

(51) Int. Cl.[7] ............................ A61M 37/00; A61M 1/36
(52) U.S. Cl. ..................... 604/6.13; 604/4.01; 604/5.01; 604/6.09; 604/6.11; 422/44
(58) Field of Search ................. 604/6.09, 6.11, 604/6.13, 4.01, 5.01, 6.15; 422/44–48; 210/742, 767, 645, 646

(56) References Cited

U.S. PATENT DOCUMENTS 4,894,164 A * 1/1990 Polaschegg ................. 210/646

(List continued on next page.)

FOREIGN PATENT DOCUMENTS

| JP | 01259871 | 10/1989 |
| JP | 05168703 | 7/1993 |
| JP | 05309132 | 11/1993 |
| JP | 8-266619 | 10/1996 |

OTHER PUBLICATIONS

Zukai:Dennetsu–Kogaku no Manabikata (Translated Abstract provided)(Illustration: How to learn heat transfer ngineering) (1$^{st}$ ed. by N. Kitayama, published by Ohmsha (Tokyo) Jul. 20, 1989, pp 104–109).

(List continued on next page.)

*Primary Examiner*—Angela D. Sykes
*Assistant Examiner*—Leslie R Deak
(74) *Attorney, Agent, or Firm*—Darby & Darby

(57) ABSTRACT

An extracorporeal circulation apparatus used for the selective temperature controlling method in which a temperature of an object is kept at a predetermined temperature, includes:

(A) a fluid replacement supply unit which quantitatively supplies a fluid replacement of which temperature has been adjusted into a blood vessel;

(B) a blood concentration unit which quantitatively withdraws blood diluted by the fluid replacement from a blood vessel and concentrates the withdrawn diluted blood; and (C) a blood supply unit which controls a temperature of the blood which has been concentrated and quantitatively supplies the concentrated blood into a blood vessel, the blood concentration unit comprising a diluted blood temperature sensor which measures a temperature of the withdrawn diluted blood, and the fluid replacement supply unit including a means which controls a temperature of the fluid replacement to be supplied based on a different extent between the measured diluted blood temperature and the predetermined temperature of the object.

31 Claims, 5 Drawing Sheets

U.S. PATENT DOCUMENTS

| | | | | |
|---|---|---|---|---|
| 5,069,662 A | * | 12/1991 | Bodden | 604/5.01 |
| 5,178,603 A | | 1/1993 | Prince | 604/6 |
| 5,344,392 A | | 9/1994 | Senninger et al. | 604/4 |
| 5,423,738 A | | 6/1995 | Robinson | 604/4 |
| 5,476,444 A | * | 12/1995 | Keeling et al. | 604/6.13 |
| 5,674,190 A | | 10/1997 | Kelly | 604/4 |
| 5,783,093 A | | 7/1998 | Holme | 210/767 |
| 5,906,588 A | * | 5/1999 | Safar et al. | 604/64 |
| 5,919,218 A | | 7/1999 | Carr | |
| 5,919,622 A | * | 7/1999 | Macho et al. | 435/6 |
| 6,336,910 B1 | * | 1/2002 | Ohta et al. | 604/6.13 |

OTHER PUBLICATIONS

Profound Hypotension with Differential Cooling of the Brain in Dogs, J. Neurosurgery, vol. 24, pp. 993–1001, (1966).

Selective Cooling of Brain Using Profound Hemodilution in Dogs, Neurosurgery, vol.. 31, No. 6, pp. 1049–1054 (12/92).

U.S. patent application Ser. No. 09/187986, filed Nov. 9, 1998.

Selective Hypothermic Perfusion of Canine Brain, Neurosurgery, vol. 38, No. 6, p. 1211–1215.

* cited by examiner

EXTRACORPOREAL CIRCULATION DEVICE AND METHOD FOR ISOLATION TEMPERATURE CONTROL METHOD

TECHNICAL FIELD

The present invention relates to an extracorporeal circulation apparatus used for various treatments in the medical field related to a mammal and especially a human, and particularly to a novel extracorporeal circulation apparatus which is usable for a case in which a selected part of a body is to be kept at a predetermined (or preset) temperature by the "selective temperature controlling (or adjusting) method" such as the "selective cooling method" or the "selective warming method." The apparatus of the present invention will be explained hereinafter with an example in a case of a human, but it is understood that the present invention is applicable to any mammal.

BACKGROUND ART

Since Woodhall introduced in 1960 a systemic profound hypothermia under a cardiac arrest for the purpose of protecting a brain against a hemorrhage or an ischemia upon a craniotomy, the systemic profound hypothermia has been employed in many types of operations. However, a pump-oxygenator employed in this method makes the procedure complicated and the blood perfusion to various organs insufficient and the method requires a large amount of heparin as an anticoagulant, resulting in problems such as a secondary cerebral hemorrhage.

One of the inventors has made an effort to overcome the problems mentioned above and has developed a method for cooling a brain selectively (which is substantially the same in its meanings as the abovmentioned "selective cooling method") while using a pump-oxygenator, and applied the method to a craniotomy (see J. Neurosurg; Vol 24, pages 993 to 1001, 1996). This selective cooling method did provide a cerebral hypotension of the brain safely, but still involved the problems with regard to the intra- and post-operative hemorrhages due to the use of a large amount of heparin still associated therewith.

In order to overcome these problems, one of the inventors discovered a method for injecting a cooled lactated Ringer's solution as a fluid replacement (or a replenisher liquid) into a cerebral artery so as to cool only a brain exclusively and to dilute a blood simultaneously while cooling the blood, resulting in a substantially reduced heparin level, whereby reducing the risk of the hemorrhage (see Neurosurgery; Vol 31, pages 0149 to 1054, 1992). This method allows a reversible extreme hypotension to be established without undergoing an oxygen deficit and enables an extreme reduction in the amount of heparin to be used as a result of introduction of the cooled fluid replacement, whereby allowing the amount of heparin to be close to that used in an ordinary angiography. In addition, the introduction of the diluted blood into a lesion leads to various safety-improving effects such as reduction in blood loss.

As described above, since the brain temperature is lowered by injecting the cooled lactated Ringer's solution. However, an amount of the lactated Ringer's solution to be injected is generally large, the injection of the lactated Ringer's solution dilutes the blood excessively and an amount of circulating blood is increased which results in the excessive body fluid condition, so that keeping the low temperature condition for a long time becomes difficult. Therefore, there is a problem in that a satisfactory low blood pressure condition (or cerebral hypotension) of the brain is not ensured. In addition to this, other problems may be occur: for example a large amount of low temperature diluted blood fills the body and a body temperature is lowered, a blood activity is lowered, balancing electrolytes in the blood becomes required, and an excessive overhydration condition may occur which cannot be attended at all with a diuretic drug.

Thus, one of the inventors studied the above problems extensively and proposed an extracorporeal circulation apparatus, which comprises (1) a fluid replacement supply unit which cools a fluid replacement (or a diluent or a replenisher liquid) and quantitatively injects the fluid replacement into a blood vessel (and thus into a body), (2) a blood concentration unit which quantitatively withdraws blood diluted by the fluid replacement from a blood vessel (and thus from the body) and concentrates the withdrawn diluted blood, and (3) a blood supply unit which quantitatively injects the concentrated blood into a blood vessel. Details of this apparatus is disclosed in Japanese Patent Kokai Publication No.9-290021. It is noted that the disclosure of the Publication is incorporated herein by the reference thereto. Using such extracorporeal circulation apparatus allows the selective cooling method to be carried out effectively.

DISCLOSURE OF INVENTION

In order to carry out the selective cooling method more smoothly, the present inventors have further studied the extracorporeal circulation apparatus which has been already proposed as described above, and have found that it is necessary for the more effective selective cooling method to more precisely control a temperature of an object which is a part of a body and to which the selective cooling method is applied (or a region of the body such as an organ, for example a brain, which is also referred to as merely "object"), and that it is important for such precise temperature control to measure a temperature of the diluted blood which is withdrawn from the interior of the body and control a temperature of the fluid replacement which is to be supplied into the interior of the body based on the measured temperature of the diluted blood when the extracorporeal circulation apparatus as described above is used, whereby the inventors have completed the present invention. That is, it has been found that the temperature of the object to which the selective cooling method is applied is more precisely controlled by measuring the temperature of the diluted blood which is withdrawn from the inside of the body and controlling the temperature of the fluid replacement which is to be supplied into the inside of the body based on the measured temperature of the diluted blood, whereby the selective cooling method is carried out more effectively.

In addition, there is a case in which it is desirable to warm an object to a predetermined temperature depending on a treatment for the object (i.e. a case of a selective warming method), and it has been found that when the object is, not cooled as described above, but warmed, the object to which the selective warming method is applied is more precisely controlled by controlling the temperature of the fluid replacement which is to be supplied into the inside of the body based on the measured temperature of the diluted blood, whereby the selective warming method is carried out more effectively.

That is, it has been found that when an selective temperature controlling method is applied in which a temperature of an object which is a part of a body is controlled to a predetermined temperature depending on a treatment for the object, the temperature of the object to which the selective temperature controlling method is applied is more precisely controlled by measuring the temperature of the diluted blood which is withdrawn from the interior of the body and controlling (or adjusting) the temperature of the fluid replacement which is to be supplied into the interior of the body based on the measured temperature of the diluted blood, whereby the selective temperature controlling method is carried out more effectively. The application of the present invention to the selective temperature controlling method will be explained hereinafter with reference mainly to the selective cooling method as an example. Since the selective warming method can be generally carried out substantially similarly to the selective cooling method except that the object is warmed in the selective warming method, those skilled in the art would readily apply the apparatus according to the present invention to the selective warming method based on the example of the selective cooling method.

It should be noted that in the extracorporeal circulation apparatus of the prior art which can be applied to the selective cooling method as described in Japanese Patent Kokai Publication No. 9-290021, the temperature measurement of the withdrawn diluted blood is not considered at all. Further, the Publication suggests that a temperature of a fluid replacement itself which is to be supplied to the interior of the body is controlled to a preset temperature by a heat exchanger through which the fluid replacement is passed depending on a temperature to which the object is to be cooled, but the temperature of the withdrawn diluted blood is not considered at all as to the temperature control of the fluid replacement. Such control of the prior art supplies the fluid replacement which has been controlled to the temperature by the heat exchanger beforehand irrespective of a condition of the object to which the selective cooling method is being applied. However, the condition of the object to which the selective cooling method is applied may change momentarily, which results in that the temperature of the object deviates from a predetermined temperature at which the object is to be kept, so that the temperature of the withdrawn diluted blood may change. For example, an organ as the object swells up and its temperature rises, and thereby the temperature of the withdrawn diluted blood may rise. In such case, in order to decrease the temperature of the organ as the object to the originally predetermined temperature so as to carry out the selective cooling method, it is necessary to lower the temperature of the fluid replacement to be supplied so as to suppress the temperature increase of the organ itself, and vice versa.

However, since the extracorporeal circulation apparatus of the prior art as described above does not take the temperature of the withdrawn diluted blood into consideration, it cannot be adapted to the condition change of the object of the selective cooling method, and thus the change of the diluted blood temperature, whereby there may be a problem in that the selective cooling method cannot be applied properly. The present invention solves such a problem.

That is, the present inventors have found that by measuring the temperature of the diluted blood which is withdrawn from the interior of the body and controlling the temperature of the fluid replacement which is to be supplied into the interior of the body based on the measured temperature of the diluted blood, the temperature control of the object to which the selective temperature controlling method such as the selective cooling method or the selective warming method is applied is carried out more precisely, so that the selective temperature controlling method is carried out more effectively.

It is noted that depending on a kind of the object to which the selective temperature controlling method is applied and a kind of treatment for the object (such as an operation, a maintenance of a low active condition or the like), a temperature at which the object is to be kept (for example, a temperature to which the object is to be cooled, or a temperature to which the object is to be warmed), namely the predetermined temperature of the object is determined upon the application of the selective temperature controlling method using the extracorporeal circulation apparatus. Therefore, the predetermined temperature at which the object is to be maintained by means of the selective temperature controlling method as well as an accuracy of such temperature maintenance is properly selected by for example a doctor depending on the treatment for the object.

Then, in the first aspect, the present invention provides an extracorporeal circulation apparatus used for the selective temperature controlling method (for example the selective cooling method and/or the selective warming method) in which a temperature of an object which is a part of a body is kept (or shifted (or changed) and kept) at a predetermined temperature ($T0$), which apparatus comprises:

(A) a fluid replacement supply unit which quantitatively supplies (or meters) a fluid replacement of which temperature has been adjusted into a blood vessel (thus into an interior of the body);

(B) a blood concentration unit which quantitatively withdraws (thus removes) blood diluted by the fluid replacement from a blood vessel (thus from an interior of the body) and concentrates the withdrawn diluted blood; and (C) a blood supply unit which controls a temperature of the blood which has been concentrated and quantitatively supplies (or meters) the concentrated blood into a blood vessel (thus into an interior of the body), the blood concentration unit comprising a diluted blood temperature sensor which measures a temperature of the withdrawn diluted blood, and the fluid replacement supply unit comprising a means which controls (or adjusts) a temperature of the fluid replacement to be supplied based on a different extent between the measured diluted blood temperature ($T1$) and the predetermined temperature of the object ($T0$) (such as a difference $\Delta T$ ($=T1-T0$), a ratio $TR$ ($=T1/T0$) or the like). It is noted that the means which controls the temperature of the fluid replacement to be supplied serves to make the different extent smaller.

By means of the apparatus as described above, the control to keep the object to which the selective temperature controlling method is applied at a temperature which is close to the predetermined temperature, and preferably substantially the predetermined temperature can be carried out more accurately, so that the selective temperature controlling method can be carried out more effectively compared with using the prior art apparatus.

In the apparatus of the present invention, the diluted blood which is withdrawn out is discharged from the object to which the selective temperature controlling method is applied, and therefore it is assumed that the temperature of the diluted blood measured by the diluted blood temperature sensor ($T1$) represents the temperature of the object to which the selective temperature controlling method is applied. The term "represent(s)" herein is intended to mean that the temperature of the diluted blood is not necessarily the temperature of the object itself (although it is preferably the temperature of the object itself), variation of the diluted blood temperature or the diluted blood temperature being relatively higher or lower corresponds to variation of the object temperature or the object temperature being higher or lower. Particularly, when the predetermined temperature at which the object is to be maintained or the accuracy of the temperature maintenance at the predetermined temperature is not so strict, the above assumption is conveniently applicable.

Further, when a supply rate of the fluid replacement is large depending on the treatment which is applied to the object so that a withdrawal rate of the diluted blood is large, a temperature change of the diluted blood during a period from the object to the diluted blood temperature sensor, and in particular a temperature change due to the body temperature may be neglected since the period required for the diluted blood to flow from the object to the outside of the body becomes short. In such case, it is often that the temperature of the withdrawn diluted blood (T1) is regarded as the temperature of the object at that time which is to be kept at the predetermined temperature (T0).

In the apparatus of the present invention, the "means which controls a temperature of the fluid replacement to be supplied based on a different extent between the measured diluted blood temperature (T1) and the predetermined temperature of the object (T0)" is a means which obtains the different extent (such as a difference or a ratio) between the measured diluted blood temperature and the predetermined temperature of the object, and increases or decreases the temperature of the fluid replacement to be supplied based on the different extent. It is noted that when there is substantially no different extent, the means keeps the temperature of the fluid replacement as it is.

Concretely, when the diluted blood temperature (T1) is higher than the predetermined temperature of the object (T0) (that is, when T1−T0>0 or T1/T0>1, and thus for example when cooling by means of the fluid replacement seems to be insufficient in the case of the selective cooling or when warming by means of the fluid replacement seems to be excessive in the case of the selective warming), the above means functions to decrease the temperature of the fluid replacement to be supplied. Such function can be achieved by forming a control system which obtains the different extent between the diluted blood temperature (T1) and based on the different extent the predetermined temperature of the object (T0) and warms and/or cools the fluid replacement to be supplied into the inside of the body so as to make the different extent smaller. The formation of such system is well known in the field of the temperature control. For example, a manner can be employed in which a set temperature of a heat exchanger (or a warming/cooing device) which controls the temperature of the fluid replacement supplied into the inside of the body is changed (that is, the set temperature is lowered) depending on the measured temperature. Also, when the diluted blood temperature (T1) is lower than the predetermined temperature of the object (T0) (that is, when T1−T0<0 or T1/T0<1, and thus for example when cooling by means of the fluid replacement seems to be excessive in the case of the selective cooling or when warming by means of the fluid replacement seems to be insufficient in the case of the selective warming), the above means functions to increase the temperature of the fluid replacement to be supplied.

It is noted that when there is substantially no different extent (that is, when T1−T0=0 or T1/T0=1, and thus for example when the selective temperature controlling method seems to be working satisfactorily), the above means functions to keep the temperature of the fluid replacement to be supplied at that time.

In a case where the temperature of the blood diluted by the fluid replacement may change after it has once reached a temperature which is the same as that of the object in the object, the above explanations are not applicable. Also, in a case where the blood diluted by the fluid replacement is withdrawn without its temperature having been thermally equilibrium with the object because of a short residence time of the fluid replacement in the object since a supply rate of the fluid replacement is too large (especially at the beginning of the fluid replacement supply), the above explanations are not applicable. If no change in T1 when the supply rate of the fluid replacement is temporarily increased and/or decreased a little, the above explanations will be applicable. It is preferable to follow the supply rate which is described concretely in the "Detailed Description of the Invention" part of the present specification.

Alternatively, when the supply rate of the fluid replacement into the inside of the body may be changed depending on the treatment for the object, it is also possible to use a means which changes the supply rate of the fluid replacement into the inside of the body in place of or in addition to the above means which adjusts the temperature of the fluid replacement. That is, it is utilized that an amount of heat transferred from the fluid replacement to the object or from the object to the fluid replacement changes when the supply rate of the fluid replacement is changed. Generally, when the supply rate is increased, an amount of heat transferred is increased. That is, when the temperature of the fluid replacement is lower than that of the object, the object is further cooled by the increase of the supply rate of the fluid replacement. Also, when the temperature of the fluid replacement is higher than that of the object, the object is further warmed by the increase of the supply rate of the fluid replacement, and when the supply rate of the fluid replacement is decreased, reversed phenomena are observed. This embodiment to change the supply rate is particularly preferably used for changing the temperature of the object a little.

In the second aspect, the extracorporeal circulation apparatus according to the present invention comprises a supplied fluid replacement temperature sensor in addition to the diluted blood temperature sensor, and the former sensor measures a temperature of the fluid replacement which is supplied to the inside of the body (a supplied fluid replacement temperature, T2). In this apparatus, an averaged value (Tav, an averaged temperature such as an arithmetical mean, a logarithmic mean, a weighted mean or the like) of the supplied fluid replacement temperature (T2) and the diluted blood temperature (T1) is assumed to be represent the temperature of the object to which the selective temperature controlling method is applied in place of the diluted blood temperature (T1) in the apparatus of the first aspect, and a different extent between the averaged temperature (Tav) and the predetermined temperature of the object (T0) is taken into consideration in place of the different extent between the diluted blood temperature (T1) and the predetermined temperature of the object (T0) in the apparatus of the fist aspect. The temperature of the fluid replacement to be supplied is controlled so that such former extent becomes smaller. The other features are substantially the same as those of the apparatus of the first aspect.

Thus, in the apparatus of the second aspect, the "means which controls a temperature of the fluid replacement to be supplied based on a different extent between the measured diluted blood temperature (T1) and the predetermined temperature of the object (T0)" in the apparatus of the first aspect is a means which obtains the different extent between the predetermined temperature of the object and the averaged temperature of the diluted blood temperature and the supplied fluid replacement temperature, and increases or decreases, or keeps the temperature of the fluid replacement to be supplied based on thus obtained different extent. That is, the different extent between the predetermined temperature and the diluted blood temperature is considered while further considering the supplied fluid replacement temperature. Similarly to the apparatus of the first aspect as described above, the supply rate change of the supplied fluid replacement may be applied in place of or in addition to the control of the fluid replacement temperature.

Concretely, when the averaged temperature (Tav) is higher than the predetermined temperature of the object (T0) (that is, when Tav−T0>0 or Tav/T0>1, and thus for example when cooling by means of the fluid replacement seems to be insufficient in the case of the selective cooling or when warming by means of the fluid replacement seems to be excessive in the case of the selective warming), the above means functions to decrease the temperature of the fluid replacement to be supplied. When the averaged temperature (Tav) is lower than the predetermined temperature of the object (T0) (that is, when Tav−T0<0 or Tav/T0<1, and thus for example when cooling by means of the fluid replacement seems to be excessive in the case of the selective cooling or when warming by means of the fluid replacement seems to be insufficient in the case of the selective warming), the above means functions to increase the temperature of the fluid replacement to be supplied. It is noted that when there is substantially no different extent (that is, when Tav−T0=0 or Tav/T0=1, and thus for example when the selective temperature controlling method seems to be working satisfactorily), the above means functions to keep the temperature of the fluid replacement to be supplied at that time.

Also, in an embodiment where the temperature of the diluted blood is changed after it has reached in the object the temperature of the object, and in an embodiment where a supply rate of the fluid replacement is too large, effects due to such embodiments are lowered in the apparatus of the second aspect.

Similarly to the apparatus of the first aspect as described before, the formation of a control system which obtains the averaged temperature (Tav) of the supplied fluid replacement temperature (T2) and the diluted blood temperature (T1), obtains the different extent between the averaged temperature (Tav) and the predetermined temperature of the object (T0), and controls the temperature and/or the supply rate of the fluid replacement to be supplied is well known to those skilled in the art.

In any aspect of the present invention, the diluted blood temperature or the averaged temperature of the diluted blood temperature and the supplied fluid replacement temperature is regarded as described above to represent and preferably be equal to the actual temperature of the object to which the selective temperature controlling method such as the selective cooling method is applied, and it is therefore preferable that the fluid replacement and the diluted blood are not so thermally affected by others as possible except the object. Thus, it is preferable that the temperatures of the fluid replacement and the diluted blood are measured as closely to the object as possible. Therefore, the temperatures of the fluid replacement and the diluted blood are measured at positions which are closest (namely, just vicinities) to the body. It is preferable that for example, the diluted blood is measured at a position which is immediately downstream of the outlet of the diluted blood from the inside of the body, and the supplied fluid replacement is measured at a position which is immediately upstream of the inlet of the supplied fluid replacement into the inside of the body.

In any aspect of the present invention, the withdrawn of the diluted blood and the supply of the fluid replacement are carried out through catheters as described below. In a particularly preferable embodiment, a thermister is located at one end of each of the catheters (one for the withdrawal of the diluted blood and the other for the supply of the fluid replacement) which end is closer to the body (i.e. the leading end when the catheter is inserted) or a vicinity of such end. Such catheters are inserted into the inside of the body so that the diluted blood temperature and the supplied fluid replacement temperature are measured while making the catheters located as near the object as possible to which the selective temperature controlling method is applied and the diluted blood temperature and the supplied fluid replacement temperature are measured, whereby the accuracy of the object temperature assumption is improved so that the accuracy of keeping the object at the predetermined temperature is improved.

In any aspect of the present invention, the apparatus according to the present invention comprises in a particularly preferable embodiment comprises a fluid replacement supply unit which cools or warms the fluid replacement to a temperature lower or higher than the body temperature and quantitatively supplies the fluid replacement into a blood vessel, a blood concentration unit which quantitatively withdraws the diluted blood from a blood vessel and concentrates the diluted blood preferably so as to reach a hematocrit value of at least 70% of that before being diluted (usually, a normal hematocrit value of a patient to whom the selective temperature controlling method is applied), and a blood supply unit which controls a temperature of the concentrated blood to a temperature near the body temperature and supplies the concentrated blood into a blood vessel.

When the selective temperature controlling method is applied using the apparatus according to the present invention, it is generally preferable to supply the fluid replacement which has been adjusted to the predetermined temperature (T0) beforehand upon starting to use the apparatus. Particularly, when the apparatus of the second aspect is used, since the supplied fluid replacement temperature (T2) is measured, it is preferable to control the temperature of the supplied fluid replacement such that T2 becomes the predetermined temperature (T0). Upon such control, it is desirable to take effects of various parameters (or factors, including a room temperature) into the consideration as described below.

In a case where the selective temperature controlling method is applied using the apparatus according to the present invention, it may be not preferable to rapidly change (for example cool or warm) the temperature of the object to the predetermined temperature (T0) when the predetermined temperature is greatly different from the temperature of the object before the application of the selective temperature controlling method (usually the body temperature in a normal condition). This is because the rapid temperature change of the object gives a certain shock, and for example electrolyte balance is broken, which may not be preferable. Thus, in such case, a manner is preferably employed in which a provisional predetermined temperature (T0-1) which is near the temperature before the application and which is between the temperature before the application and the predetermined temperature is set so that the temperature of the object reaches T0-1 first, then a next provisional predetermined temperature (T0-2) is set by shifting the provisional temperature toward the predetermined temperature a little so that the temperature of the object reaches T0-2, and then an additional next provisional predetermined temperature is set if necessary, . . . , and the temperature of the object finally approaches the original predetermined temperature (T0) in steps.

For example, in a case in which the object is to be cooled from 37° C. to 25° C. as the predetermined temperature (T0), the provisional predetermined temperature (T0-1) is first set at 35° C. so that the object temperature reaches 35° C., then the next provisional predetermined temperature (T0-2) is set at 33° C. when the object temperature approaches or reaches 35° C. so that the object temperature reaches 33° C., . . . , whereby the object temperature thus approaches 25° C. as the original predetermined temperature (T0) in steps. The manner in which the object temperature approaches the predetermined temperature may be stepwise as described above or continuous. When the object temperature is raised reversely, the above is applicable similarly. When the object is warmed, similar is applicable. It is of course possible to rapidly cool or warm if no problem occurs when the object temperature is changed to the predetermined temperature rapidly.

When the object temperature is adjusted to the predetermined temperature (T0) by applying the apparatus of the present invention to the selected object, in one embodiment a temperature of the fluid replacement to be supplied is controlled first by means of a fluid replacement temperature controller such that the temperature of the fluid replacement to be supplied becomes T0 (which may be the provisional temperature as the above). The fluid replacement thus controlled is supplied into the inside of the body.

When the apparatus of the first aspect is used for the supply of such fluid replacement, the diluted blood temperature (T1) is measured, and then the fluid replacement temperature controller which has been set at the predetermined temperature (T0) is re-set based on the measurement of the diluted blood temperature, that is the temperature of the fluid replacement to be supplied in the fluid replacement temperature controller is re-adjusted (namely, the temperature is set higher or lower than T0 or the temperature is kept). Also, when the apparatus of the second aspect is used, the supplied fluid replacement temperature (T2) is further measured followed by obtaining the average temperature of the supplied fluid replacement temperature (T2) and the diluted blood temperature (T1), and then the averaged temperature is compared with the predetermined temperature (T0) followed by controlling the fluid replacement temperature controller again. It is noted that with regard to the predetermined temperature (T0), it may be preferable to set a provisional predetermined temperature, based on which the fluid replacement temperature controller is adjusted followed by gradually shift the provisional predetermined temperature so that the original predetermined temperature is finally reached as described above.

After having made the object temperature reach the predetermined temperature, returning the object temperature to the original object temperature (that is, recovering the object temperature) truly corresponds to warming the object to the predetermined temperature. Therefore, the apparatus according to the present invention may be used for a temperature recovering method in which a temperature of the object is returned to its original temperature of the object which has been shifted to the predetermined temperature by the selective temperature controlling method. That is, the selective warming method after carrying out the selective cooling method or vice verse may be carried out by using the same apparatus.

It is noted in a case in which the object temperature is shifted to the predetermined temperature, and in particular the object is warmed, that it may be preferable to use oxygen containing blood when the object needs oxygen for the purpose of its metabolism. That is, it may be preferable that not using for example a Ringer's solution as the fluid replacement, at least a portion and optionally most of the fluid replacement is replaced with blood (autologous blood or transfusion blood) as described below. When the blood is supplied as above, it is preferable that the blood is oxygen oxygenated by for example an artificial lung. In this embodiment, warming is applicable to a case in which the object is warmed from its normal temperature to a higher temperature as well as a case in which the object is returned from its selectively cooled temperature to its original normal body temperature.

It is noted that the present invention also provides an extracorporeal circulation method for the selective temperature controlling method. The former method is an extracorporeal circulation method for keeping an object at a predetermined temperature for the selective temperature controlling method, which comprises the steps of:

(A) quantitatively supplying (or metering) fluid replacement of which temperature has been adjusted into a blood vessel by means of a fluid replacement supply unit;

(B) quantitatively withdrawing blood diluted by the fluid replacement from a blood vessel and concentrating the withdrawn blood by means of a blood concentration unit; and (C) controlling a temperature of the blood which has been concentrated and quantitatively supplying the blood into a blood vessel by a blood supply unit, and the method being characterized in that a temperature of the withdrawn diluted blood is measured by means of the blood concentration unit, and a temperature of the fluid replacement which is quantitatively supplied by the fluid replacement supply unit is controlled based on a different extent between the measured diluted blood temperature and the predetermined temperature of the object.

The fluid replacement supply unit measures the temperature of the fluid replacement to be quantitatively supplied and may control the temperature of the fluid replacement based on a different extent between the predetermined temperature and an averaged temperature of the supplied fluid replacement temperature and the diluted blood temperature in place of the different extent between the measured diluted blood temperature and the predetermined temperature of the object.

Also, temperature control of the fluid replacement to be quantitatively supplied is preferably carried out while considering heat transfer between the fluid replacement and a surrounding of the apparatus until the fluid replacement is supplied into the blood vessel. In addition, it is preferable that the temperature of the fluid replacement to be quantitatively supplied has been adjusted to the predetermined temperature of the object when starting the above method. In other words, the present invention provides an extracorporeal circulation method in which the extracorporeal apparatus according to the present invention as described above or described in detail below is used.

LIST OF NUMERALS

Figure 1:
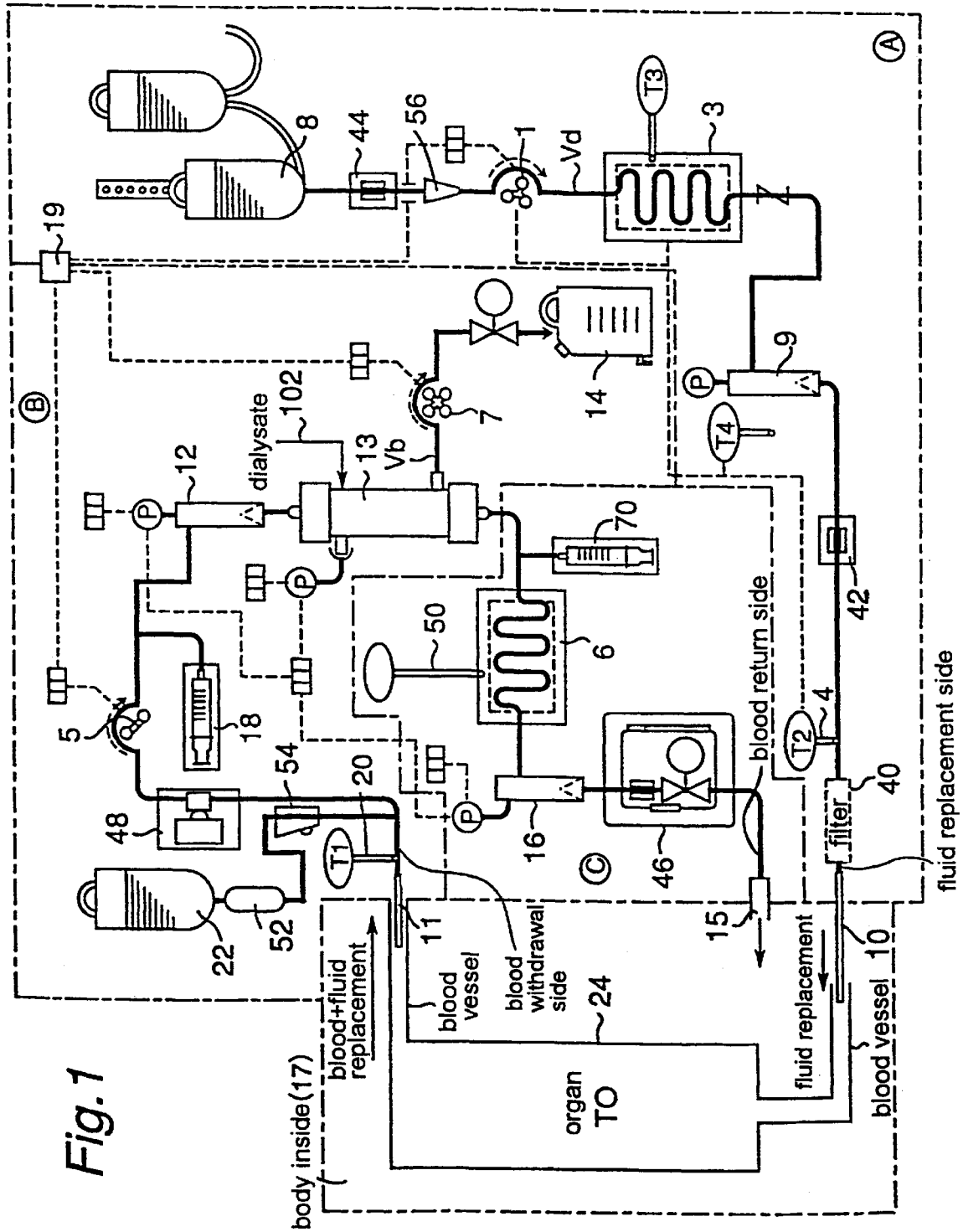
FIG. 1 is a schematic drawing which shows the apparatus according to the present invention.

1 . . . liquid supply pump, 3 heat exchanger,
4 . . . supplied fluid replacement temperature sensor,
5 . . . withdrawal pump, 6 . . . heat exchanger,
7 . . . water removal pump,
8 . . . fluid replacement container, 9 . . . drip chamber,
10, 11 . . . catheter, 12 . . . drip chamber,
13 . . . blood concentration element,
14 . . . removed water tank, 15 . . . catheter, 17 . . . body,
18 . . . heparin supplier,
19 . . . supply/removal controlling mechanism,
20 . . . diluted blood temperature sensor,
24 . . . object, 100 bypass line, 102 . . . dialysate.

DETAILED DESCRIPTION OF THE INVENTION

The term "selective temperature controlling (or adjusting) methods" is a method which shifts a temperature of an object as a part of a body to a predetermined temperature so as to keep the object in a condition in which a predetermined purpose can be achieved, and which includes the "selective cooling method" and "selective warming method." Also, the "selective temperature controlling method" includes a method in which the temperature of the object is returned to its original temperature thereafter. The term "selective cooling method" is a method which is used in a medical treatment field, and particularly in a brain surgery field, and it concretely means a method wherein a part of a body as the object (for example, an organ such as a brain) is selected and that part is locally cooled. The selective cooling method is a locally cooling method used for example in a case in which bleeding is expected (for example a case of an operation of a limited part of a body (for example, a head)) or a case in which a metabolism or an activity of an organism function is suppressed locally and temporarily during which various procedures or treatments are carried out. While the "selective cooling method" is to cool the object, the "selective warming method" is merely different in that the object is warmed, and it is applicable for the treatment of for example a cancer, a frostbite or the like. As described above, temperature recovery after cooling may be included by the selective warming method. Further, the temperature recovery after warming may also be included by the selective cooling method.

The present invention is based on the following concept: The fluid replacement of which temperature has been adjusted is injected through a blood vessel into an artery at a certain position thereof which directly or indirectly leads to the object of which temperature is to be controlled, the blood diluted by the fluid replacement is withdrawn through a blood vessel from a vein at a certain position thereof which directly or indirectly leads to the object, then the diluted blood is concentrated so as to recover the blood which is similar to before being diluted and preferably which is substantially equivalent to the blood before being diluted, and the recovered blood is returned through a blood vessel to a vein at a position thereof closer to a heart (so-called a heart side position) which directly or indirectly leads to said vein from which the diluted blood is withdrawn after a temperature of the recovered blood is adjusted (for example returned to a temperature of the human body), so that a temperature of the object is safely and selectively adjusted to the predetermined temperature without changing and preferably without substantially increasing an amount of body fluid kept in the body.

For example, when the selective cooling method is applied to a brain, the fluid replacement is supplied at a neck portion into an arteria vertebralis, the diluted blood is withdrawn from a jugular vein, and the concentrated blood is returned into the inside of the body through for example a femoral artery. Also, for example for the application to liver, the fluid replacement is supplied through a hepatic artery, the diluted blood is withdrawn from an appropriate vein, and the concentrated blood is returned into the body at a position of a vein closer to the heart which directly or indirectly connects to said appropriate vein. Generally, the fluid replacement is supplied to an artery which belongs to the object to which the selective cooling method is applied. The vein from which the diluted blood is withdrawn is preferably closely related to an artery which belongs to the object (and thus the vein collects a large amount and preferably the largest amount of the blood which has passed through said artery). Although the position at which the concentrated blood is returned is not particularly limited, generally the position is at the vein. When this vain is the same as the vein from which the diluted blood is withdrawn, the concentrated blood is returned to a position closer to the heart. In order that a temperature change of the diluted blood as small as possible after it has reached the object temperature, the diluted blood is preferably withdrawn from a position which is as close to the object as possible.

By carrying out the selective cooling method using the apparatus according to the present invention, problems such as a troublesome operation of a heart-lung machine under a cardiac arrest, and various risks such as bleeding are solved while avoiding for example extreme overhydration, so that a cerebral hypotension condition (for example, a local low irrigation condition) is stably ensured.

In the apparatus according to the present invention, the concentrated blood temperature is adjusted before it is returned to the body inside, and such adjustment is preferably carried out by heat exchange, and particularly by indirect heat exchange. An apparatus having a heater and/or a cooler for that purpose is not particularly limited. In any case, it is possible that the predetermined temperature of the concentrated blood is achieved by immersing a conduit through which the concentrated blood flows in a constant-temperature bath set at a predetermined temperature, and such heat exchanging manner is preferable. In one embodiment, when it has been known beforehand that only warming or cooling is carried out, the heat exchanger may comprise only a heater or a cooler.

The fluid replacement (or a diluent) used in the present apparatus is not particularly limited as far as it is able to be cooled or warmed in an appropriate manner, and it is able to be used for cooling or warming the object in the body while it is supplied into the body through a blood vessel so as to dilute the blood. Generally, the fluid replacement at least does not effect adversely the intended treatment, and preferably the fluid replacement helps such treatment. Concretely, an aqueous solution which contains a nutrient and/or an electrolyte may be exemplified as the fluid replacement, and an isotonic solution such as a Ringer's solution, a lactated Ringer's solution, a Ringer's solution containing a low molecular dextrin (for example containing 5%) or the like is preferably used as the fluid replacement, but not limited thereto.

In one embodiment, the apparatus according to the present invention comprises a fluid replacement temperature controller as the means to adjust a temperature of the fluid replacement to be supplied. The controller may be the indirect heat exchanger as described above, and for example one in which an appropriate liquid (which is usually water) as a heat transfer medium is charged in a vessel equipped with a heater or a cooler and a tube which supplies the fluid replacement is located in the liquid in for example a spiral form may be used. By controlling a temperature of the liquid using the heater and/or cooler, the temperature of the fluid replacement at the exit of the fluid replacement temperature controller (T3) can be controlled.

It is noted that when a liquid such as the fluid replacement, blood or the like is warmed and/or cooled, the apparatus comprising a heating means (for example, an electric resistive heater) and/or a cooling means (for example, a cooler using a coolant) may be used as described above, and in a preferable embodiment, an warming/cooling apparatus comprising a Peltier element is used. It is noted that warming includes a case in which a temperature is returned to an original temperature after cooling, and that cooling includes a case in which a temperature is returned to an original temperature after warming, both of which may be referred to as temperature returning.

The warming/cooling apparatus comprising the Peltier element warms or cools depending on an electric current direction (thus, polarity) across the element, and a thermal dose upon warming or cooling depends on an amperage. When the Peltier element is used, switching between warming and cooling may be carried out freely electrically and the amperage may be increased and decreased easily and precisely so that response and sensitivity of the temperature control are good and the temperature control is accurate. The Peltier element has been known for a long time, it has not known or done that its advantage is very conveniently utilized when the features of the element are combined in the extracorporeal circulation apparatus which may be used for various treatments in the medical field.

For example, the temperature of the fluid replacement, the blood or the like immediately after leaving the warming and/cooling apparatus is measured, and the measured result is fed back to a controller of the warming and/cooling apparatus, so that increase or decrease of an amount of the electric current through the Peltier element and switching of its polarity may be carried out with a good sensitivity and accuracy. The body condition of a patient who uses the extracorporeal circulation apparatus may change momentarily, and when the apparatus according to the present invention is used, such change can be detected through T1. Thus, it is preferable that an extent of warming/cooling of the fluid replacement to be supplied into the body, the blood to be returned to the body or the like is freely changed and switching between warming and cooling is freely carried out, and in order to be thus preferable, the warming/cooling apparatus comprising the Pertier element is preferably used, which is particularly preferable for controlling the temperature recovery.

More particularly, when an electric current is passed across the Peltier element, one junction thereof fevers to be at a higher temperature and the other junction thereof absorbs heat to be a lower temperature, and when the polarity of the voltage applied to the Peltier element is reversed, the temperature relationship between the junctions is reversed. Usually, one junction is warmed or cooled by using air at a room temperature, and for example by blowing air using a fan so that a thermal energy is transferred between the junctions. Usually, thus warmed or cooled junction is contacted with the fluid replacement, the blood or the like indirectly (for example through a plastic film, a metal thin film or the like) for the heat exchange. Using the warming/cooling apparatus comprising the Peltier element as described above results in compactness of the extracorporeal circulation apparatus, space saving, improved operability and so on may be achieved.

The fluid replacement which leaves the fluid replacement temperature controller flows through a certain length of a conduit until supplied into the body, during which a temperature of the fluid replacement is affected by a temperature of its surrounding circumstance (i.e. a room temperature) so that the supplied fluid replacement temperature (T2) is often different from the temperature of the fluid replacement upon leaving the fluid replacement temperature controller (T3). For example, when the surrounding temperature is higher than the temperature of the fluid replacement upon leaving the fluid replacement temperature controller (T3), T2 is higher than T3, and when the surrounding temperature is lower, T2 is lower than T3. Therefore, there is usually a substantive temperature difference $\Delta T$ ($=T3-T2$) is present. In the present apparatus, it is preferable to take this temperature difference $\Delta T$ into account when the fluid replacement temperature is adjusted based on the different extent between the average temperature of the diluted blood temperature (T1) and the supplied fluid replacement temperature (T2) and the predetermined temperature (T0). That is, in a preferable embodiment according to the present invention, the temperature of the fluid replacement temperature controller (T3) is controlled considering the temperature change of the fluid replacement between leaving the fluid replacement temperature controller and going into the body, namely the heat absorption from or the heat radiation into the surrounding circumstance of the apparatus.

Usually, the temperature difference is affected by parameters such as operation conditions of the apparatus (for example, a kind of the fluid replacement and its supply rate, a material of the conduit for supplying the fluid replacement and a diameter of the conduit), the temperature of the circumstance surrounding the apparatus (i.e. a room temperature, T4) and so on. Therefore, when relationships between the temperature difference $\Delta T$ and the parameters have been obtained beforehand as calibration curves by varying the parameters variously, it can be seen which temperature should be set in the fluid replacement temperature controller (T3) so as to achieve an aimed T2 under specific parameter conditions. Since T2=T0 is generally preferable at the beginning of the operation, T3 may be obtained based on the temperature difference between the T2(=T0) and T1 in the initial stage of the operation.

Particularly, in the apparatus according to the second aspect in which the diluted blood temperature (T1) and the supplied fluid replacement temperature (T2) are measured, the average of these temperature is assumed to be the object temperature, the different extent between the average and T0 is considered and T2 is selected such that the different extent becomes smaller. Upon such selection, the temperature difference (ΔT) is considered and the set temperature of the fluid replacement temperature controller (T3) is selected (=T2+ΔT), so that the temperature (T2) can be precisely controlled.

That is, since the diluted blood temperature (T1) is measured and the predetermined temperature of the object T0 is determined beforehand, T2 which lowers the different extent is obtained by for example T2=2T0−T1. Further, ΔT can be obtained with reference to the calibration curves which were obtained under the specific parameter conditions, and the set temperature of the fluid replacement temperature controller (T3) may be obtained by T3=T2+ΔT considering the obtained T2 and ΔT, and the fluid replacement temperature controller is set at thus obtained T3.

In order to obtain a temperature of a liquid which is flowing through a length of a conduit while considering the heat transfer to its surrounding circumstance, various model equations are conceivable, and any model equation may be used as for as it does not substantially affect the applied selective temperature controlling method adversely. Concretely, the following model equation for example may be used in place of the calibration curves as described above, so that the heat transfer between the liquid and its surrounding circumstance is considered so as to obtain the set temperature of the fluid replacement temperature controller (T3):

$$T3 = T2 - a \int_0^{l/v} (T4 - Tt) t\, dt \qquad \text{Equation (I)}$$

(wherein l is a length (m) of the conduit between the fluid replacement temperature controller and a position at which a supplied fluid replacement temperature is measured, Tt is a temperature (°C.) of the fluid replacement at a time of t (second) supplied into the body, v is a supply rate (linear velocity, m/s) of the fluid replacement, and $a = \alpha A/V$ (wherein α is a heat transfer coefficient (W/m²K) of a material of the conduit, A is a total surface area (m²) of the conduit, and V is a volume (m³) of the fluid replacement in the conduit)). It is noted that Equation (I) has been obtained from a general equation of the heat transfer.

In one case, the fluid replacement temperature Tt may be regarded to change linearly during the fluid replacement flows between the fluid replacement temperature controller and the position at which the supplied fluid replacement temperature is measured. In such case, the fluid replacement temperature Tt can be expressed by the following equation:

$$Tt = T3 + t(T2 - T3)/(l/v)$$

By substituting this equation in the above integral expression equation followed by numerical calculation, the temperature of the fluid replacement controller (T3) may be obtained as to the aimed T2. Other equation which can express Tt may be similarly used so as to obtain the temperature of the fluid replacement controller (T3).

Alternatively, in place of the above Equation (I), the following equation (II) may be used:

$$T3 = T4 - (T4 - T2)e^{b/v} \qquad \text{Equation (II)}$$

in which $b = 4\alpha a l/(\rho d C p)$ (wherein a is a heat transfer coefficient (W/m²K) of a material of the conduit, l is a length (m) of a conduit between the fluid replacement temperature controller and the position at which the supplied fluid replacement temperature is measured, ρ is a specific gravity (kg/m³) of the fluid replacement, d is an outer diameter (m) of the conduit, Cp is a specific heat capacity (J/kg·K) of the fluid replacement, and v is a supply rate (linear velocity, m/s) of the fluid replacement) This equation may be obtained by forming a differential equation which expresses that an amount of heat loss of the fluid replacement into its surrounding during the fluid replacement flows over a very small length is equivalent to an amount of heat gain by the surrounding, solving the differential equation and integrating using boundary conditions that the fluid replacement temperature is T3 and T2 when the length of the conduit is zero and 1, respectively. It is noted that those skilled in the art can derive this equation easily with reference to for example "Zukai: Dennetu-kogaku no Manabikata (Illustration: How to learn heat transfer engineering)" (1st edition, by N.Kitayama, published by Ohmsha (Tokyo), Jul. 20, 1989, pp 104–109).

The apparatus according to the first aspect does not measure the supplied fluid replacement temperature (T2), but the heat transfer between the fluid replacement and the surrounding until the fluid replacement of which temperature has been adjusted is supplied into the blood vessel is considered upon controlling the temperature of the fluid replacement to be supplied. That is, when the fluid replacement temperature which has been adjusted is expected to become increased until the entry of the body, the fluid replacement is adjusted to be lower beforehand by such temperature increase (which is thus similar to ΔT). In the opposite case, the fluid replacement is adjusted to be higher beforehand by ΔT.

In one preferable embodiment, the apparatus according to the present invention comprises an artificial lung which can oxygenate the fluid replacement, the blood and/or the diluted blood to be supplied to the body. The artificial lung may be any device which has a function to increase an amount of dissolved oxygen in the fluid replacement, the blood or the diluted blood, so-called an oxygen addition function or an oxygenation function, and for example a membrane type and a bubbling type may be used. In a particularly preferable embodiment, a portion of the diluted blood is divided into a side stream without being concentrated and supplied to the artificial lung where it is oxygenated, and the oxygenated diluted blood is supplied into the body again together with the fluid replacement after subjected to the temperature adjustment by the fluid replacement temperature controller. In an alternative preferable embodiment, the fluid replacement is introduced to the artificial lung where it is oxygenated, and then supplied into the body.

In one of other preferable embodiments (for example in a case where the object to which the selective temperature controlling method is applied metabolizes), the apparatus according to the present invention supplies to the body, in place of the fluid replacement as described above, autologous blood drawn from a patient to be treated and/or transfusion blood together with the fluid replacement. Upon such supply, the autologous blood and/or the transfusion blood is preferably introduced to the artificial lung where it is oxygenated. In other embodiment, it is possible to oxygenate by providing, in place of such artificial lung, a chamber which holds a liquid such as the diluted blood, the fluid replacement or the blood and by bubbling the liquid with oxygen (or air) while blowing it into the liquid.

In the apparatus of the present invention, the concentration of the diluted blood means that a hematocrit value of the diluted blood drawn from the body (thus which value is smaller than a hematocrit value of original (i.e. before being diluted) blood) is increased or recovered, and concretely it is carried out by filtration or dialysis (hereinafter which are generically referred to as a filtration treatment). The filtration treatment may be carried out by a hemofilter, a dialyzer or the like which is generally used as an artificial kidney. In the apparatus according to the present invention, the blood after being concentrated has a hematocrit value of usually at least about 70% of, preferably at least about 90% of, more preferably at least about 95% of and most preferably substantially the same as that of the blood before being diluted.

When the dialyzer (or dialysis device) is used for the concentration of the diluted blood in the apparatus of the present invention, there is an advantage that balance of electrolytes and/or nutrients of the patient to whom the selective temperature controlling method is applied can be kept, or the balance which has been destroyed can be recovered since dialysate contains the electrolytes and/or the nutrients which are transferred to the diluted blood and excessive electrolytes and/or waste products which are not required by the body are removed by the dialysate. Thus, the blood concentration unit may be preferably a hemodialysis device (including a continuous hemodialysis (CHD) device), or a hemodiafiltration device (including a continuous hemodiafiltration (CHDF) device).

In fact, in a certain embodiment in which the apparatus according to the present invention is used, a hematocrit value of a normal person (about 40 to 50%) is generally diluted to a hematocrit value of about 5 to 20%, for example about 7%, and such hematocrit value of the diluted blood is recovered up to about 30 to 50% after being concentrated. Therefore, a hematocrit value recovery ratio (a hematocrit value after concentrated/a hematocrit value before concentrated) is about 0.7 to 1.00.

One embodiment of the apparatus of the present invention is an extracorporeal circulation apparatus for carrying out the selective cooling method which is used for selectively cooling a region of the object to the predetermined temperature. Also, in other embodiment, there is provided an extracorporeal circulation apparatus which is used for carrying out the selective, not cooling, but warming method to the predetermined temperature. Such apparatus may be used for warming the object to a high temperature at which a cancer cell may be killed but a normal cell is not affected. Concretely, it has been found that the cancer cell is killed at about 42° C., and the apparatus may be used for warming only an object in which such cell are present.

The present invention will be explained hereinafter in detail with reference to the accompanying drawings.

FIG. 1 is a diagram (flow sheet) which schematically shows the extracorporeal circulation apparatus of the present invention, which comprises (A) the fluid replacement supply unit, (B) the blood concentration unit and (C) the blood supply unit (these units are delimited by the alternate long and short dash lines).

The fluid replacement supply unit (A) comprises a fluid replacement container (8), a fluid replacement pump (1) (with functions of metering a pumping rate and its adjustment) which supplies the fluid replacement into the body (17), a fluid replacement temperature controller (3) and a drip chamber for fluid replacement (9), and the temperature of the fluid replacement which is supplied into the body (T2) is measured by a supplied fluid replacement temperature sensor (4).

Also, the shown extracorporeal circulation apparatus comprises the blood concentration unit (B), which comprises a blood pump (5) which draws the diluted blood from the body (17) (i.e. carries out the blood removal), and finally returns recovered concentrated blood into the body (17), an anticoagulant (such as heparin, fusan or the like) supplier (18), a drip chamber for blood (12), a blood concentration device such as a filter for filtration (or a dialyzer) (13), and a removed water tank (14), and optionally a water removal pump (7), and the temperature of the drawn diluted blood (T1) is measured by a diluted blood temperature sensor (20). It is noted that a fluid replacement tank (22) is provided in the blood concentration unit so as to fill conduits and elements in the apparatus with the fluid replacement upon starting the apparatus operation.

Further, the shown extracorporeal circulation apparatus comprises the blood supply unit (C) which comprises a drip chamber for blood to be returned (16) and a heat exchanger (6) for adjusting the temperature of the concentrated blood. In order to control the temperature of the concentrated blood, the heat exchanger has a temperature sensor (50).

Appropriate conduits (such as a silicone tube, a polyvinyl chloride tube or the like, shown with thicker lines in the drawing) connect between those units or elements which constitute the units, and required connections between the body (17) and each units are formed by means of catheters (10, 11 and 15).

In the fluid replacement supply unit (A), the fluid replacement pump (1) quantitatively injects into the body (17) the fluid replacement usually at 10 to 800 ml/min., preferably 50 to 500 ml/min. and more preferably 100 to 400 ml/min. A practical supply rate of the pump is appropriately selected within those ranges depending on a purpose of the treatment for the object. As the pump which can quantitatively deliver (thus meter) the fluid replacement, a roller pump may be exemplified which is often used for the delivery of blood. It is noted that in order to carry out the speedy temperature adjustment of the object, the supply rate are preferably relatively large, and for example a supply rate in the range 100 to 400 ml/min. is further preferably used (particularly in the case of a brain of an adult as the object in the selective cooling method). In place of the roller pump, a centrifugal pump may be used, wherein an appropriate flow rate control means such as a valve, an inverter function or the like is preferably combined.

When the supply rate of the fluid replacement is controlled by for example a motor rotational speed of the fluid replacement pump (1), a flow meter is not necessarily provided as an additional element, but it may be located in a fluid replacement line so as to confirm the supply rate of the fluid replacement. The flow meter may be for example a electromagnetic flow meter. Further, the pump preferably has a control function which makes the supply rate as predetermined when it is not so (for example, a function to change the rotational speed of the pump motor (such as an inverter function) or a function to change a pressure loss of a conduit (such as a valve)). When the quantitative supply of the fluid replacement pump (1) is ensured, the flow meter may be omitted, and in this sense, the shown apparatus has no flow meter. Generally, a flow meter may be provided in any conduit through which a fluid has to be supplied at a predetermined flow rate, and combination of the flow meter with a pump ensures a predetermined flow rate (thus quantitative draw or supply). As to the other pumps (5 and 7), the same as to the pump (1) is applicable except the flow rate ranges as described above.

The container (8) may be a plastic vessel or bag in which the fluid replacement is enclosed, or may be a tank in which the fluid replacement taken out from such container is stored. There are provided the drip chamber (56) and a fluid empty detector (44) between the container (8) and the pump (1). The fluid replacement supply unit may further include in addition to the above described elements, other drip chamber (9, having a pressure gauge P) for the removal of bubbles, which removes the bubbles entrained with the fluid replacement. Similar drip chambers (12 and 16) are provided in the blood concentration unit and the blood supply unit, respectively. It is noted that a filter (40) may be provided so as to remove contaminants in the fluid replacement and a bubble detector (42) may be provided for check the presence of the bubbles in the fluid replacement.

The apparatus according to the present invention comprises the blood concentration unit which quantitatively withdraws the diluted blood from a blood vessel and usually a vein through which the diluted blood flows after passing the object, and concentrates the diluted blood preferably to an original hematocrit value of the blood. Such unit requires a withdrawal supply pump (5) which quantitatively withdraws the diluted blood from the body (17) and supplies and finally returns the blood into the body and an element (13) which concentrates the diluted blood which is withdrawn and supplied thereto. It is noted that in addition to the fluid replacement, blood is supplied to the object through the blood vessel to which the fluid replacement is supplied and the other blood vessels, so that the blood which leaves the object is in a condition diluted by the fluid replacement. Optionally, a balloon catheter may be inserted into only an artery which leads to the object so as to substantially stop the blood flow and only the fluid replacement is supplied to the object, and the fluid replacement may be supplied through the catheter. Also, as to the withdrawal of the diluted blood, a balloon catheter may be inserted into only a vein which leads from the object so as to withdraw substantially all the diluted blood to outside of the body.

The pump (5) preferably quantitatively withdraws the diluted blood through the catheter (11) at a rate in the range usually 10 to 600 ml/min., preferably 50 to 400 ml/min., and more preferably 80 to 300 ml/min. from the body (particularly in the case of a brain of an adult as the object in the selective cooling method). The practical flow rate of the pump (5) may be selected as required within such ranges depending on a purpose of the treatment. As the pump (5), one which is of the same type of that of the fluid replacement pump (1) may be used, and it may be cooperated with a flow meter (not shown) as described above.

Upon using the apparatus of the present invention, the diluted blood is drawn by means of the catheter (11) through a vein from the region to be selectively cooled, and it is introduced through the liquid transport pump (5) to a blood side inlet of the blood concentration element (13) which is preferably a disposable product.

In the apparatus of the present invention, the concentration element (13) is preferably a dialysis device (in which a dialysate (102) is supplied to the concentration element (13) as shown) or a filtration device as described above, and the control of the element is preferably carried out based on the hematocrit values as measures before the blood is diluted and after the blood is concentrated. Measurement of the hematocrit value may be conducted by obtaining a volume percentage (%) of red blood cells after the concentrated blood is subjected a centrifugation treatment.

It is convenient to measure a flow rate of the supplied fluid replacement and a flow rate of liquid discharged out from the concentration element (13) (which is also referred to as "filtrate") as well as a total amount of the fluid replacement which has been supplied and a total amount of the filtrate which has been discharged, and to control a patient not to be in an excessive overhydration condition or not to be in an excessive dehydration condition, and usually such control is sufficient. It is noted that when the dialysis device is used as the concentration element (13), an amount of the dialysate which has been supplied to the dialysis device is included in an amount of the filtrate, and thus such amount of the dialysate has to be deducted from the amount of the filtrate.

The concentration element (13) may include a pump (7) on its filtrate side when necessary, so that a pressure difference across the concentration element (13) can be further increased (and thus a controllable range of the filtration pressure (or a pressure difference upon the dialysis operation) is enlarged), whereby a filtrate rate becomes more versatile due to using the pump (7). The concentration element (13) of course dehydrates by means of only the pressure difference produced by the pump (5) between the diluted blood side (a delivery pressure) and the permeate side (atmospheric pressure) produced by the pump (5), which is so-called natural filtration or natural dehydration (or water removal). In the case of the natural dehydration, the filtrate is collected in the filtrate container (14) without passing through the pump (7).

When the pump (1) is running, the filtrate rate from the concentration element (13) (Vb ml/min., provided that supply rate of the dialysate is deducted from Vb in the case of the dialysis operation) is preferably substantially smaller than a supply rate of the fluid replacement supplied into the body (Vd ml/min.) so that a hematocrit value of the blood in the body is kept not higher than before the beginning of the treatment. This is based on an idea that in order to make the temperature adjusting effect by means of the fluid replacement effective, it is preferable to temporarily keep a certain amount of the fluid replacement within the region of the object. Therefore, in a preferable embodiment of the apparatus according to the present invention, the flow rates are controlled to satisfy the relationship of $0.1Vd \leq Vb \leq Vd$ (wherein $Vd \neq 0$). When Vb is smaller than 0.1Vd (i.e. Vb<0.1Vd), an amount of the body fluid is considerably excessive temporarily, which is not preferable. On the other hand, when Vb is substantially larger than Vd, excessive concentration of the blood occurs, which is not preferable. However, Vb being larger than Vd is not completely excluded in the apparatus of the present invention, and Vb may be larger than Vd if no adverse effect occurs in the treatment where the apparatus of the present invention is used.

In the apparatus of the present invention, the fluid replacement is made of an aqueous solution of a low molecular material (such as an electrolyte, a saccharide (for example glucose)) as a main component. A total amount of the filtrate (provided that an amount of the dialysate is deducted in the case of the dialysis device as the concentration element) during the operation of the apparatus of the present invention is most preferably substantially the same as a total amount of the fluid replacement which has been supplied during the operation, which means that operation times of the pump (1) and the pump (5) and optionally the pump (7) may be different, and that even though the pump (1) is being stopped, the pump (5) may be being operated so that Vb is a some substantive rate under the consideration of the preferable relationship of $0.1Vd \leq Vb \leq Vd$ as described above. The total amount of the filtrate (provided that an amount of the dialysate is deducted in the case of the dialysis device as the concentration element) is not necessarily substantially the same as the total amount of the supplied fluid replacement, these amounts may be different as far as no problem occurs during the treatment. From such viewpoint, it is generally sufficient to keep a relationship of for example 0.8×total amount of filtrate (provided that an amount of the dialysate is deducted in the case of the dialysis device as the concentration element)≦total amount of supplied fluid replacement≦1.2×total amount of filtrate (provided that an amount of the dialysate is deducted in the case of the dialysis device as the concentration element). Since a certain time is required for the fluid replacement to be discharged after passing the cooled object, the pumps (5) and (7) of course do not have to be started simultaneously with the operation start of the pump (1). It is noted that during a practical treatment or procedure, the supplied fluid replacement may be discharged as urine, which is included by the total amount of the filtrate in the present specification. That is, the urine is regarded to be the filtrate and the above relationship is considered (provided that a rate of the urine is not included in the filtrate rate Vb).

In the shown embodiment of the apparatus, the blood pump (5) has a function to withdraw the diluted blood from the body (17), a function to supply the diluted blood to the concentration element (13) so as to allow the concentration of the diluted blood and a function to return the concentrated blood to the body (17) thereafter. It is obvious for those skilled in the art that these functions may also be achieved by separate pumps while providing inbetween buffers (or reservoirs)

In the blood concentration unit of the apparatus of the present invention may include the drip chamber (12) for the removal of bubbles and the anticoagulant supply element (18), for example a heparin supply device. It is noted that the anticoagulant (for example, heparin, fusan or the like) may supplied at any suitable position in the apparatus of the present invention. In the shown embodiment, the heparin supply device (18) is located in the blood concentration unit, and the supplied heparin does not substantially transfer to the filtrate even though it passes through the blood concentration element (13) (namely, remaining in the concentrated blood).

The apparatus of the present invention comprises the blood supply unit which adjusts the temperature of the concentrated blood which may be at a higher or lower temperature to around a normal body temperature, and supplies such blood into a blood vessel (vein). Concretely, the unit comprises a heat exchanger for warming/cooling (6) which may be able to adjust the blood to for example around 37° C. and supply it to usually a vein at a position which is closer to the heart. In the concrete, upon using the apparatus according to the present invention, the concentrated blood passes the heat exchanger (6) through a conduit which is connected to an blood outlet of the blood concentration device (13), and injected into the vein through the catheter (15). In this case, there may be provided a protamine supply pump (70), a drip chamber for bubble removal (16) and a bubble detector (46).

In a preferable embodiment of the present invention, a supply/removal (dehydration) control mechanism (19) is provided which automatically controls each of the flow rate of the supplied fluid replacement Vd, the flow rate of the withdrawn diluted blood, and the flow rate of the filtrate Vb so as to keep a body fluid amount as desired based on the balance of the flow rates. When the urine is discharged, the control of the balance may be carried out while considering an amount of the urine. When the supply/removal control mechanism (19) is used in the apparatus of the present invention, the flow rate of the supplied fluid replacement, the flow rate of the withdrawn blood, and the flow rate of the filtrate (thus, delivery rates of the pumps (1), (5) and (7), the last rate including a rate of the dialysate) should have to be in controlled conditions along with a purpose of the treatment in which the apparatus is used. That is, the pumps (1) and (5) and optionally the pump (7) should be cooperated as shown with the broken lines such that Vb and Vd satisfy the ranges for them as described above, the relationship between Vb and Vd as described above and the relationship between the total amount of the filtrate (provided that an amount of the dialysate is deducted in the case of the dialysis device as the concentration element) and the total amount of the supplied fluid replacement as described above. Such control is well known to those skilled in the art and employed in an operation of an artificial kidney. It is noted that in place of the pump (7), other pump may be located on the concentrated blood side of the blood concentration element (13) (i.e. downstream of the concentration element).

For example, it is not necessarily required that the filtrate of which amount corresponds to an amount of the supplied fluid replacement is immediately discharged. Of course, it may be possible so, but it is preferable that the fluid replacement is held in the body for a certain period so as to achieve the purpose of the treatment in which the selective temperature controlling method is carried out, and then withdrawn gradually from the body so as to avoid the excessive overhydration of the body fluid. Vb and Vd are preferably controlled by the supply/removal control mechanism (19) so as to achieve such purpose.

Alternatively, hematocrit values of the withdrawn diluted blood and/or the concentrated blood are measured on line using a non-contact type hematocrit measuring device, and the supply/removal control mechanism (19) controls the flow rates of the pumps (1), (5) and (7) based on the measurements of the hematocrit values so as to keep the hematocrit value of the diluted blood for example not smaller than 5% and/or to keep the hematocrit value of the concentrated blood for example at least 40%.

The extracorporeal circulation apparatus shown in the drawings are able to be used in the selective temperature controlling method for example as described below which will be explained by an example of the selective cooling:

Case 1

Fluid replacement is charged beforehand from a fluid replacement tank (22) into the elements and the conduits in the apparatus. First, an object (24) to which the selective cooling method is applied, a predetermined temperature (T0) to which the object is cooled depending on a treatment for the object, and operation conditions such as a supplied fluid replacement rate, a withdrawn diluted blood rate and so on are determined. Then, a heat exchanger (3) is operated, and its adjusting temperature (T3) is set at for example the predetermined temperature (T0). Upon this, the adjusting temperature (T3) may be shifted a little from the predetermined temperature (T0) considering the heat absorption or heat loss after leaving the heat exchanger (3) until entering the body (namely, ΔT) as well as the temperature change after entering the body until reaching the object.

Each catheter is inserted into the body, and the pump (1) is operated and the fluid replacement is supplied from the fluid replacement tank (8) to the heat exchanger (3), whereby the fluid replacement temperature is adjusted to or near the predetermined temperature (T0) and the fluid replacement is supplied into the body. Simultaneously or a predetermined period later, the pump (5) withdraws the diluted blood from the body, and the temperature thereof (T1) is measured by the temperature sensor (20). The diluted blood is supplied to the blood concentration element (13) where the blood is separated by means of filtration. Upon filtration, the dehydration (or water removal) pump (7) may be optionally operated so as to help the blood concentration. The blood concentrated by means of the filtration is passed through the heat exchanger (6) so as to heat to a predetermined temperature and then returned into the body through the catheter (15).

The above operation is carried out in the case where the measured diluted blood temperature (T1) may be regarded to represent an actual temperature of the region of the object, and thus the different extent between T1 and the predetermined temperature of the object region (T0), for example the difference $\Delta Ta$ (=T1−T0) is obtained. When $\Delta Ta>0$, it means that the object has not been sufficiently cooled, and thus an operation to lower the set temperature (T3) of the heat exchanger (3) is carried out, which may be manually or automatically.

On the other hand, when $\Delta Ta<0$, it means that the object has been excessively cooled, and an operation to raise the set temperature (T3) of the heat exchanger (3) is carried out. Thereafter, the diluted blood temperature is measured again, and $\Delta Ta$ is obtained similarly. Based on the obtained $\Delta Ta$, the set temperature (T3) of the heat exchanger (3) is changed. The time interval between the first calculation of $\Delta Ta$ and the second calculation of $\Delta Ta$ is not particularly limited, but when it is excessively long, the diluted blood temperature (T1) is likely to hunt, so that the interval is preferably short. It is of course possible that the diluted blood temperature (T1) is continuously measured, so that the set temperature (T3) of the heat exchanger (3) is considered while considering a characteristic of the temperature difference $\Delta Ta$ therefrom (such as an absolute value of the temperature difference, a change rate with time of the temperature difference or the like). The measurement and the change of the set temperature (T3) of the heat exchanger (3) as described above are repeated such that $\Delta Ta$ becomes smaller whereby the diluted blood temperature (T1) approaches the predetermined temperature of the object (T0) and such temperature is kept. It is noted that when $\Delta Ta$ is substantially zero, the set temperature (T3) of the heat exchanger (3) does not particularly have to be changed.

Case 2

Although in Case 1, only the diluted blood temperature (T1) is taken into account, the supplied fluid replacement temperature (T2) is also considered in addition to the diluted blood temperature (T1) in Case 2. In this case, the averaged temperature Tav of T1 and T2 (=(T1+T2)/2) may be regarded to indicate the actual temperature of the object (T0), and this case is generally superior to Case 1 wherein only T1 is considered in the estimation of the object temperature. Similarly to Case 1 before, the different extent between the averaged temperature (Tav) and the predetermined temperature of the object region (T0), for example the difference $\Delta Tb$ (=(T1−T2)/2−T0) is obtained. The others are substantially the same as those in Case 1. It is noted that T1 and T2 have the same weight in the above so as to obtain the averaged value, but it may be possible to change their weights. For example, it is possible to use 1.5×T1 in place of T1, and 0.5×T2 in place of T2. Particularly since T1 is affected by the object temperature, it may be preferable that T2 is regarded to be heavier.

When $\Delta Tb>0$, it means that the object has not been sufficiently cooled, and thus an operation to lower the set temperature (T3) of the heat exchanger (3) is carried out. On the other hand, when $\Delta Tb<0$, it means that the object has been excessively cooled, and an operation to raise the set temperature (T3) of the heat exchanger (3) is carried out. Thereafter, the measurement is repeated, and Tav and $\Delta Tb$ are made approach the predetermined temperature T0 and zero, respectively similarly to Case 1, which conditions are kept.

Case 3

Temperature control of the heat exchanger (3) may be carried out in various appropriate manners depending on the different extent, for example the value of the difference $\Delta Ta$ or $\Delta Tb$.

For example, when the difference $\Delta Ta$ is positive in Case 1, the adjust temperature of the heat exchanger (3) is operated so as to lower the diluted blood temperature (T1). When the difference $\Delta Ta$ is negative, the opposite operation is carried out. Upon these operations, it is preferable to consider a static characteristic and/or a dynamic characteristic of the difference $\Delta Ta$.

For example, when the difference $\Delta Tb$ is positive in Case 2, the adjust temperature of the heat exchanger (3) is operated so as to lower the supplied fluid replacement temperature (T2). Upon this operation, considering that the difference $\Delta Tb$ desirably becomes zero, T2 is calculated from the predetermined temperature (T0) and the measured diluted blood temperature through an equation: T2=2T0−T1. The calculated T2 is used as the set temperature of the heat exchanger (3). In other embodiment, the set temperature (T3) of the heat exchanger (3) is determined based on the calculated T2 through the calibration curves or the above equation (I) under consideration of the heat exchange with the surrounding from the heat exchanger (3) to the temperature measurement position of the supplied fluid replacement. As seen from the equation, T3 varies depending on the supply rate of the fluid replacement (v). In the treatment which is carried out using the selective cooling method, v is usually not an arbitrary value, but has been determined beforehand within an acceptable range (for example v is in an range within which no damage is given to an inner wall of a blood vessel). Therefore, the acceptable value of v is preferentially determined, and then other parameter values are determined depending on the apparatus to be used so that T3 is finally determined.

Upon using the apparatus of the present invention, the fluid replacement flows from its container (8) through the supply pump (1) to the heat exchanger for the fluid replacement temperature adjustment (3) where its temperature is adjusted, and then injected by means of the catheter (10) into the body through a blood vessel, usually an artery which leads to the object to which the selective temperature adjusting method is applied. The catheter is inserted into the blood vessel (vein) which leads to the object to which the selective temperature adjusting method is applied, and the position at which the catheter is inserted is not necessarily near the object. It may be possible to employ a method such as a so-called Seldinger's method with which a catheter is transdermally inserted into for example a femoral artery up to a brain followed by supplying the fluid replacement.

In such case, it is preferable not to locate the supplied fluid replacement temperature sensor (4) outside the body but to locate it at a tip or vicinity thereof of a leading end of the catheter (10) upon the insertion thereof, so that a temperature of the supplied fluid replacement (T2') may be measured at a position which is closer to the object region (i.e. at a more distal position). As a result, T2' is used in place of T2 which is used for the estimation of the temperature of the object region in Case 2 as the above. Similarly, as to the withdrawal of the diluted blood from the object region, the leading end of the catheter is inserted as close to the object region as possible and the temperature sensor is located at a tip or vicinity thereof of a leading end of the catheter, so that a temperature of the diluted blood (T1') can be measured at a position which is closer to the object region.

Figure 5:
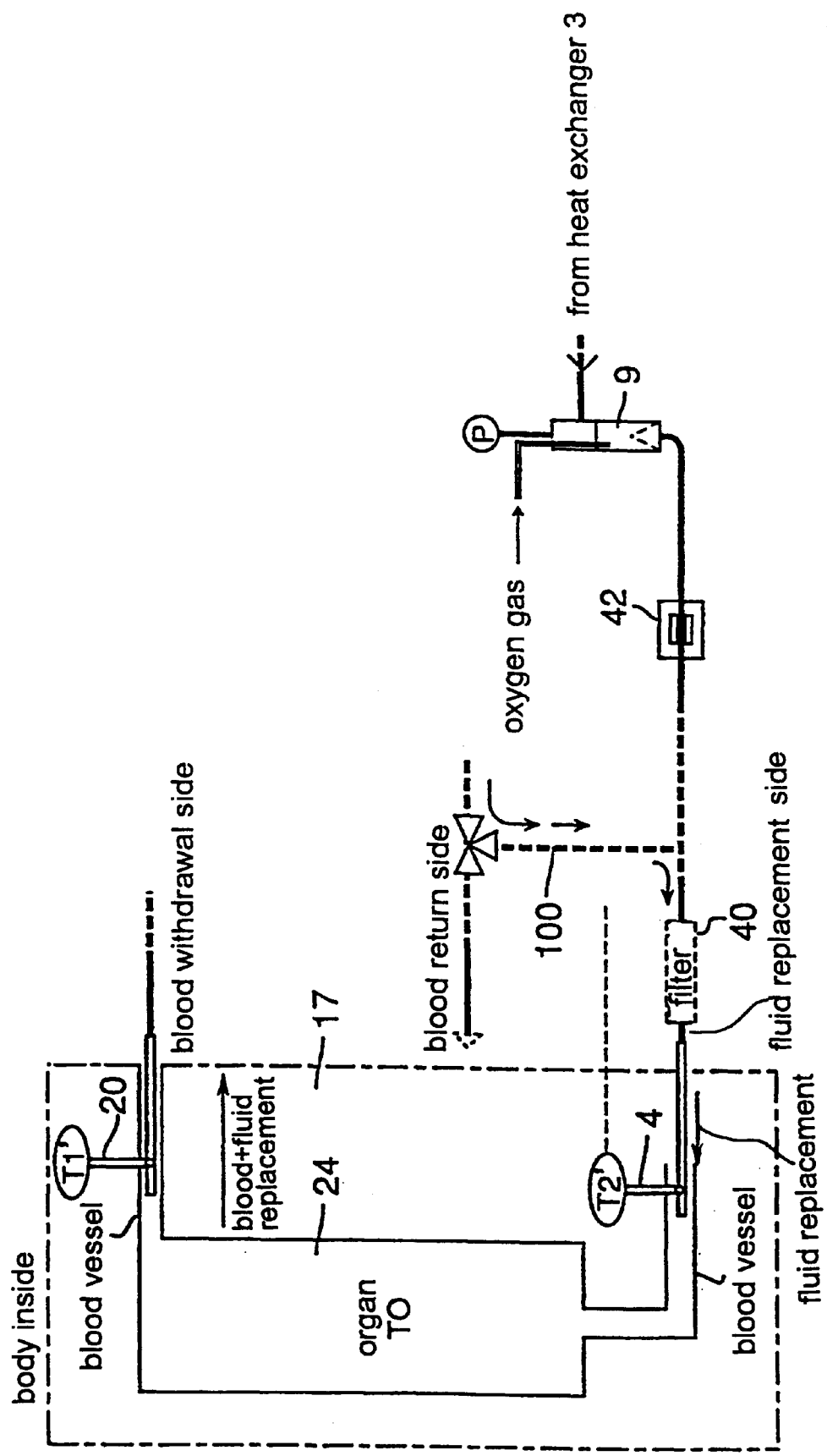
FIG. 5 is a schematic drawing of the apparatus shown in FIG. 1 which comprises in place of an artificial lung, a drip chamber for bubbling oxygen gas.

Therefore, by locating the temperature sensor at the tip of the leading end of the inserted catheter, accuracy of the estimation of the object region temperature is further improved, so that the selective temperature controlling method is effectively carried out. That is, T1' is used in place of T1 in Case 1, and T1' and T2' are used in place of T1 and T2 in Case 2, so that the temperature estimation of the object region is further reliable. It is noted that an embodiment involving T1' and T2' is schematically shown in FIG. 5.

In the embodiment shown in FIG. 1, a blood pressure measuring element (48) for the withdrawn diluted blood pressure, is located before the pump (5), and a drip chamber (52) and a cramp (54) are located downstream of the fluid replacement tank (22).

In a preferable embodiment, the apparatus of the present invention further comprises an artificial lung which oxygenates the diluted blood, the fluid replacement, the autologous blood and/or the transfusion blood.

Figure 2:
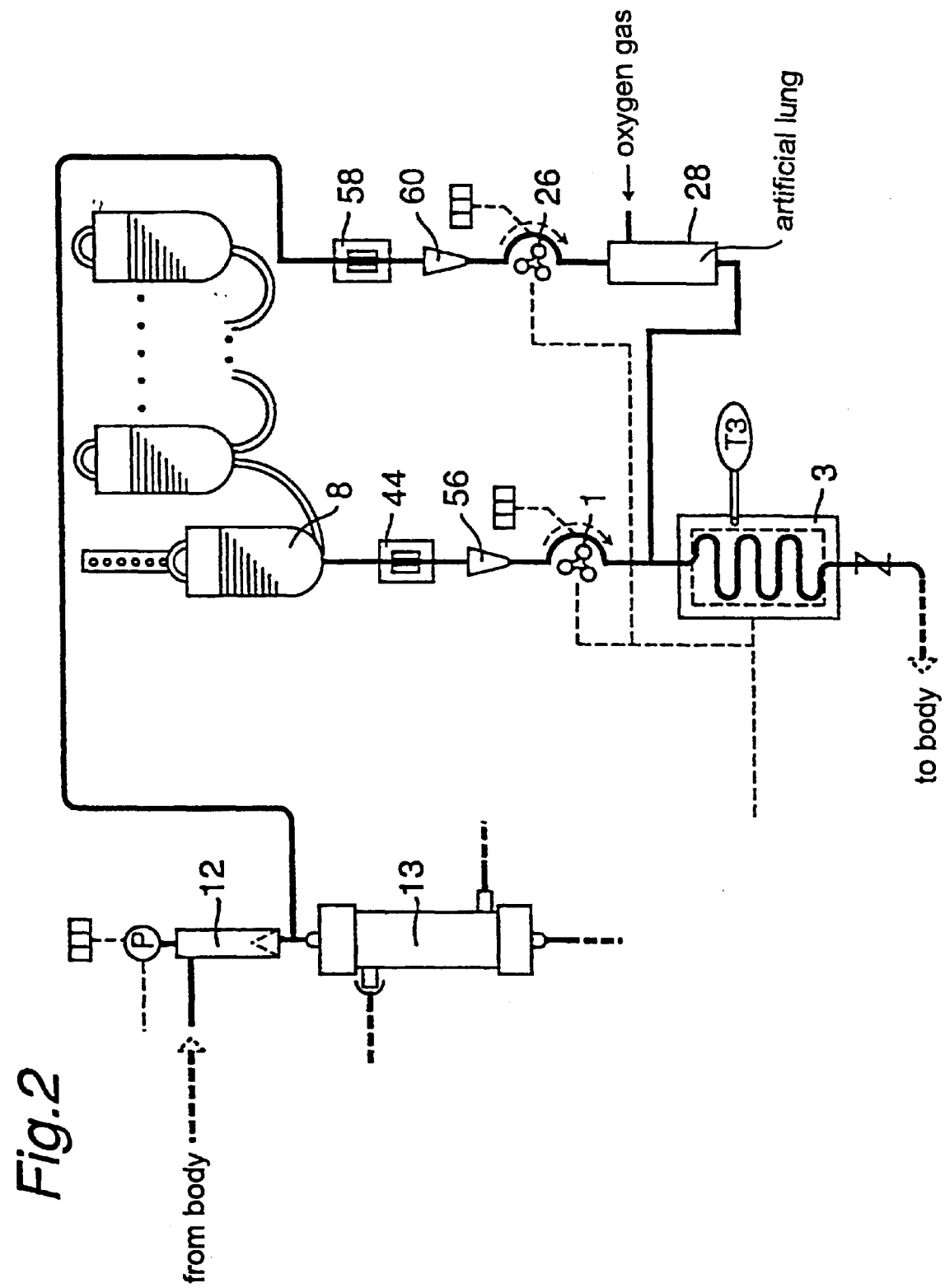
FIG. 2 is a schematic drawing of the apparatus shown in FIG. 1 which further comprises an artificial lung for oxygenating a portion of diluted blood (only a part of the lung being shown)

In FIG. 2, the apparatus of the present invention which includes a configuration which oxygenates a portion of the diluted blood withdrawn from the body is schematically shown (only a portion of such configuration is shown and the other portions are substantially the same as those in FIG. 1 except that configuration). In the shown embodiment, a portion of the diluted blood drawn from the body is divided before the diluted blood supplied to the concentration element (13) by the pump (26), and such portion is supplied to the artificial lung (28) through a liquid empty detector (58) and a drip chamber (60). Oxygen is supplied to the artificial lung (28). The diluted blood leaving the artificial lung (28) is merged to the fluid replacement which is freshly supplied, followed by passing through the heat exchanger (3) and thereafter to the body (17).

Figure 3:
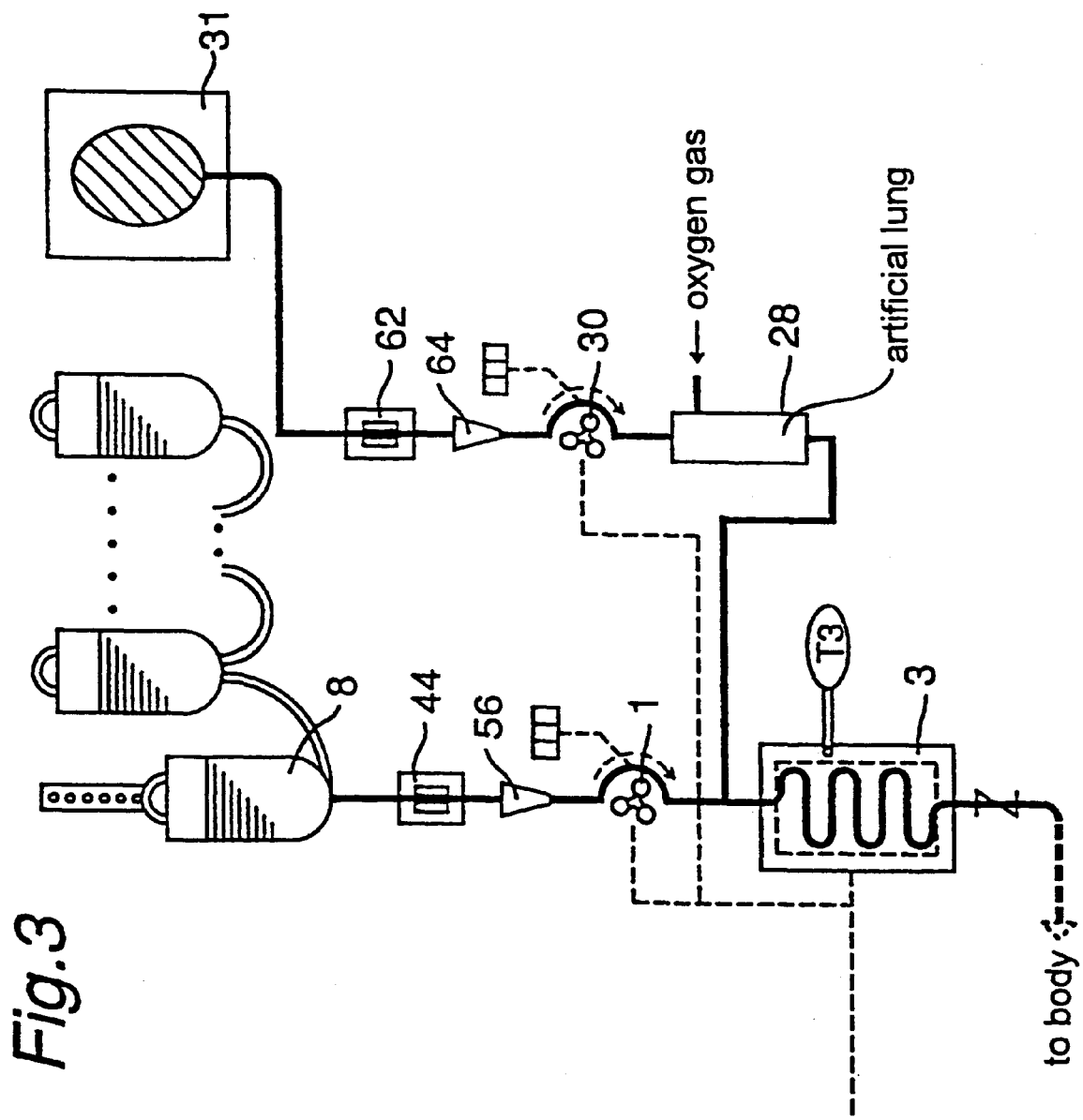
FIG. 3 is a schematic drawing of the apparatus shown in FIG. 1 which further comprises an artificial lung for oxygenating autologous blood or transfusion blood (only a part of the lung being shown)

In the embodiment shown in FIG. 3, autologous blood beforehand obtained from a patient to be treated and/or transfusion blood (31) is supplied to the body through the artificial lung (28). Similarly to FIG. 2, FIG. 3 shows only a portion which is different from that of FIG. 1. The autologous blood or the transfusion blood is passed to the artificial lung (28) through a liquid empty detector (62) and a drip chamber (64) by a pump (30), and thereafter merged to the fluid replacement which is freshly supplied, followed by passing through the heat exchanger (3) and thereafter to the body (17).

Figure 4:
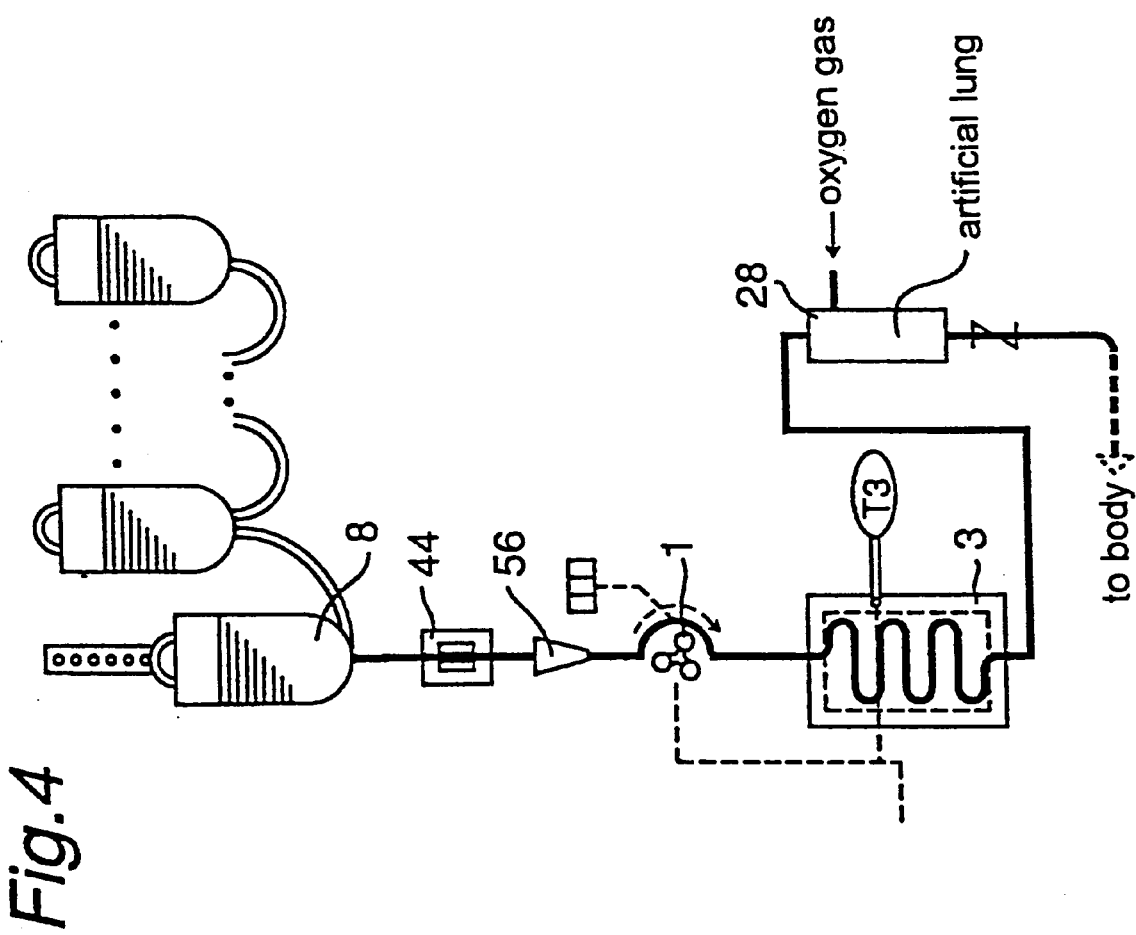
FIG. 4 is a schematic drawing of the apparatus shown in FIG. 1 which further comprises an artificial lung for oxygenating fluid replacement (only a part of the lung being shown)

In the embodiment shown in FIG. 4, the fluid replacement which is to be supplied to the body is supplied to the artificial lung (28) after it leaves the heat exchanger (3), followed by passing to the body. It is noted that the configurations other than that shown in FIG. 4 are substantially the same as those in FIG. 1.

In addition to or in place of the artificial lung as described above, it is possible that oxygen gas is supplied to a drip chamber (9) which is located before the body after the heat exchanger (3) in a supply line for the fluid replacement, so that oxygen is bubbled in the fluid replacement (optionally including the autologous blood or the transfusion blood) passing through the drip chamber so as to oxygenate it.

It is noted that FIG. 5 also shows an embodiment in which the conduit exiting the heat exchanger or warming/cooling device (6) is connected to the fluid supply conduit. In such embodiment, when the selected object has been cooled to the predetermined temperature, the required treatment has been carried out, and then the object is returned to its original temperature (namely, upon the temperature recovery), an operation is carried out such that at least a portion of the concentrated and recovered blood is supplied to the object together with the fluid replacement. The temperature recovery is substantially the same as warming the selected object using the apparatus according to the present invention, and thus the temperature recovery operation may be carried out by the selective warming method using the apparatus of the present invention. On the other hand, when the selected object has been warmed to a predetermined temperature, the required treatment has been carried out, and then the object is returned to its original temperature (namely, upon the temperature recovery), the temperature recovery operation may be carried out by the selective cooling method using the apparatus of the present invention.

Upon the temperature recovery, when the object temperature is raised, the metabolism function of the object is accelerated so that supply of oxygen may be desirable. In such case, it is preferable to replace at least a portion of the fluid replacement which is to be supplied to the body with blood, and supply them to the object. In that case, a bypass line 100 (shown with the broken line) is provided as shown in FIG. 5 so that at least a portion of the concentrated blood is divided after the temperature adjustment, and supplied together with the fluid replacement. Usually, when the object temperature is increased, the metabolism is accelerated, so that the object requires a more amount of oxygen. Thus, it is preferable to gradually increase an amount of the concentrated blood to be divided while an amount of the fluid replacement is gradually reduced. It may be preferable that only the blood is supplied finally and the supply of the fluid replacement is stopped. In such case, it is preferable that the blood is oxygenated by for example the artificial lung. Upon such temperature recovery, the object temperature is estimated based on the measured diluted blood temperature (T1, which is a drawn blood temperature when the supply of the fluid replacement is stopped) and the measured supplied fluid replacement temperature (T2, which may be a supplied blood temperature when the supply of the fluid replacement is stopped) while the supplied fluid replacement temperature and the divided recovered blood temperature are controlled. It is noted that upon the provision of the bypass line 100, it is preferable that a valve or the like is located so as to supply a total amount or a portion of the concentrated and recovered blood to the fluid replacement supply conduit, whereby a volume of the blood to be returned to the body directly (i.e. blood return side) and a volume of the blood to be supplied to the object together with the fluid replacement (i.e. fluid replacement side) are appropriately divided. In addition, it is possible that for example a Y-shaped coupler is located beforehand in a conduit of the fluid replacement, and the catheter (15) is pulled out and connected to the Y-shaped coupler so that the blood return conduit is directly connected to the conduit of the fluid replacement, whereby a total amount of the blood is supplied to the fluid replacement side. Further, the catheter (15) pulled out may be inserted into the drip chamber (9) for the fluid replacement.

Effects of the Invention

By using any of the embodiments of the apparatus according to the present invention, the object to which the selective temperature controlling method is applied is able to be kept in a desired temperature condition with an improved accuracy. Particularly, when the position for the temperature measurement is close to the object, namely the temperature measurement is carried out most closely to the body, the accuracy is further improved. Especially, when the temperature sensor is located at around the leading tip of the catheter which is inserted into the blood vessel, the accuracy becomes remarkable. Thus, the advantages of the selective temperature controlling method can be further remarkable.

The apparatus of the present invention may be used for a case in which the selective temperature controlling method is applied upon any of surgical operations. For example, by cooling an affected part in a brain, a breast, an abdominal part, an extremity or the like to a predetermined temperature accurately by means of the fluid replacement, activity of for example the organ is suppressed and a progress of a trauma (for example, damage of a tissue due to ischemia) is avoided, operation safety is increased by forming a hypotension condition (for example, a low irrigation condition), and reduction of an amount of used heparin as well as an amount of the transfusion blood, so that an operation becomes possible without a risk of infection due to the blood transfusion.

In addition, using the apparatus of the present invention, the selective temperature controlling method as the selective cooling method is used not only during an operation but may be employed as a part of a method to control a condition, and particularly control a low active condition of a patient. That is, by accurately keeping an affected part in a diluted blood condition at a desired temperature (which includes keeping at a body temperature (normal temperature)), the progress of illness may be delayed or prevented.

For example, when a part of the body is wished to be cooled to a certain extent, for example to a temperature within a range of about 34 to 15° C. and preferably rapidly, but the other parts are not wished to be cooled to such low temperature (for example not wished to be lower than 28° C.), only that part can be cooled rapidly and accurately by using the apparatus of the present invention. As an example, there is a case in which before a treatment of a brain bruise, only a brain is to be cooled rapidly so as to delay (or reduce) swelling of the brain, but the other parts are not to be cooled.

Particularly, the apparatus of the present invention cools only a part of the body and the other parts are not so cooled, and only the part of the body is able to be kept at a very low temperature accurately while the body as a whole is kept at a relatively higher temperature (or a normal temperature) by adjusting the temperature and the supply rate of the fluid replacement. This means that only the brain can be cooled rapidly during a treatment of brain contusion because of for example a traffic accident, which is very effective to a craniotomy operation. In addition, since the apparatus of the present invention cools only a part of the body while the other parts are cooled not so much, no side effect occurs, so that the part of the body may be kept at the low temperature for an extended period.

Further, when the fluid replacement is supplied using the apparatus of the present invention, a part of the body is temperature controlled while the blood is diluted. In the case of the selective cooling method, since the metabolism of that part is suppressed by cooling (thus, oxygen consumption of the cooled tissue is reduced, namely the low active condition is kept), it is sufficient that only the diluted blood is supplied to such tissue. Therefore, upon the operation of such part, only the diluted blood flows the part, so that an amount of hemorrhage is greatly reduced.

The present invention provides the apparatus which is used for the condition control as described above, namely the condition control apparatus. In the present specification, the condition control is used to mean to keep a limited part or a whole body of a patient at a predetermined temperature, for example to keep in a low active condition at a low temperature, or to keep in a condition at a warmed temperature such that a low body temperature condition due to hypothermia is improved or malignant cells are killed, whereby controlling so as to delay or prevent progress of the illness. Particularly, in the latter condition control, accurate temperature keeping of the object is very important (especially, an excessive high temperature should be avoided) from a viewpoint of the protection of the normal cells, and in this sense, the apparatus of the present invention which is able to keep the object at the predetermined temperature accurately is very effective.

As explained at the beginning, the apparatus of the present invention is applicable to the treatment for an animal including a human. The conditions (including the numerical values) and the embodiment disclosed in the present specification are generally used for such a treatment, and more appropriate embodiments may be selected by repeating experiments depending on concrete cases.

Upon such selection, as parameters with which the apparatus of the present invention is controlled, data of a patient (such as a body weight, a hematocrit value, an object to be treated and the like), data of cooling and warming which has been collected up to now (such as a kind and a temperature of a fluid replacement, a supplied fluid replacement rate, a region to be cooled and its temperature change with time, a withdrawn diluted blood rate, a temperature change of the other parts with time and the like), a kind of treatment (such as a part to be treated, a treatment method, a treatment time and the like), and data of a filtration device (such as a kind of filter medium, a filtration pressure, a filtration rate and the like). Those various data are collected upon the experiments, which are then numerically analyzed (regressed), so that they can be used for the practical treatment.

Further, when the artificial lung is provided in the extracorporeal circulation apparatus of the present invention, there is provided an advantage in that an operation time is extended by the oxygenation of the fluid replacement.

What is claimed is:

1. An extracorporeal circulation apparatus for a selective temperature controlling method in which the temperature of an object is kept at a predetermined temperature, comprising:

(A) a fluid replacement supply unit which quantitatively supplies a fluid replacement into a blood vessel wherein said fluid replacement supply unit comprises a means for controlling the temperature of the fluid replacement based on a different extent between:
  (1) the measured diluted blood temperature and
  (2) the predetermined temperature of the object;

(B) a blood concentration unit which quantitatively withdraws blood diluted by the fluid replacement from a blood vessel and concentrates the withdrawn diluted blood wherein said blood concentration unit comprises:
a diluted blood temperature sensor which measures the temperature of the withdrawn diluted blood; and
a filtration means for separating out filtrate; and (C) a blood supply unit which controls a temperature of the blood which has been concentrated and quantitatively supplies the concentrated blood into a blood vessel.

2. An extracorporeal circulation apparatus, according to claim 1, wherein:

the control of the temperature of the fluid replacement to be supplied is carried out considering heat transfer between the fluid replacement and a surrounding of the apparatus until the fluid replacement of which temperature has been adjusted is supplied into the blood vessel.

3. An extracorporeal circulation apparatus, according to claim 2, wherein:

the control of the means which controls the temperature of the fluid replacement is carried out based on Equation (I):

$$T3=T2-a\int_0^{l/v}(T4-Tt)tdt \qquad \text{Equation (I)}$$

(wherein T2 is the temperature of the supplied fluid replacement, T3 is a set temperature of the means which controls the temperature of the fluid replacement, T4 is a room temperature, l is the length of a conduit from the means which controls the temperature of the fluid replacement to the supplied fluid replacement temperature sensor, Tt is a temperature of the fluid replacement at a time t, v is a supply rate of the fluid replacement, and a=αA/V, α is a heat transfer coefficient of a material of the conduit, A is a total surface area of the conduit, and V is a volume of the fluid replacement of the conduit).

4. An extracorporeal circulation apparatus, according to claim 1, wherein:
the supplied fluid replacement is injected into the blood vessel through an artificial lung.

5. An extracorporeal circulation apparatus, according to claim 4, further comprising, in place of the artificial lung, a drip chamber into which oxygen is injected.

6. An extracorporeal circulation apparatus, according to claim 1, wherein:
a portion of the withdrawn diluted blood is injected into the blood vessel together with the fluid replacement to be injected after the withdrawn diluted blood passes through an artificial lung.

7. An extracorporeal circulation apparatus, according to claim 1, wherein:
the fluid replacement supply unit supplies autologous blood or transfusion blood together with the fluid replacement, and the autologous blood or the transfusion blood is supplied through an artificial lung together with the fluid replacement into the blood vessel.

8. An extracorporeal circulation apparatus, according to claim 1, wherein:
a temperature of the supplied fluid replacement has been adjusted to a temperature within a temperature range of 36.5 C. to 3 C. and the fluid replacement is used for the selective cooling method.

9. An extracorporeal circulation apparatus, according to claim 1, wherein:
a temperature of the supplied fluid replacement has been adjusted to a temperature within a temperature range of 36.5 C. to 42 C. and the fluid replacement is used for the selective warming method.

10. An extracorporeal circulation apparatus, according to claim 1, wherein:
a flow rate of the injected fluid replacement Vd is 10 to 600 ml/min., preferably 50 to 500 ml/min., and more preferably 100 to 400 ml/min., and the blood concentration unit comprises a filtration unit which is controlled such that a flow rate of filtrate Vb is 10 to 200 ml/min., preferably 50 to 170 ml/min., and more preferably 100 to 140 mil/min.

11. An extracorporeal circulation apparatus, according to claim 1, wherein:
the blood concentration unit concentrates the diluted blood to a hematocrit value of at least 70% of that before being diluted.

12. An extracorporeal circulation apparatus, according to claim 1, further comprising:
a means for controlling the flow rates of the supplied fluid replacement, the withdrawn diluted blood, and the filtrate.

13. An extracorporeal circulation apparatus, according to claim 1, wherein:
the blood concentration unit comprises a dialysis device.

14. An extracorporeal circulation apparatus, according to claim 1, wherein:
the means which controls the temperature of the supplied fluid replacement comprises a Peltier element.

15. An extracorporeal circulation apparatus, according to claim 1, wherein:
the selective temperature controlling method is a selective cooling method or a selective warming method.

16. An extracorporeal circulation apparatus, according to claim 1, wherein:
the selective temperature controlling method is a temperature recovery method after a selective cooling method or after a selective warming method.

17. An extracorporeal circulation apparatus, according to claim 1, wherein:
the apparatus is used for a surgical operation.

18. An extracorporeal circulation apparatus, according to claim 1, wherein:
the apparatus is used for controlling a condition of a part of a body.

19. An extracorporeal circulation apparatus for a selective temperature controlling method in which the temperature of an object is kept at a predetermined temperature, comprising:
(A) a fluid replacement supply unit which quantitatively supplies fluid replacement into a blood vessel wherein:
said fluid replacement supply unit comprises a temperature sensor which measures the temperature of the supplied fluid replacement;
said fluid replacement supply unit comprises a means for controlling the temperature of the fluid replacement based on a different extent between:
(1) an averaged temperature of the measured supplied fluid replacement temperature and the measured diluted blood temperature, and
(2) the predetermined temperature of the object;
(B) a blood concentration unit which quantitatively withdraws blood diluted by the fluid replacement from a blood vessel and concentrates the withdrawn diluted blood;
wherein said blood concentration unit comprises a diluted blood temperature sensor which measures the temperature of the withdrawn diluted blood; and
(C) a blood supply unit which controls a temperature of the blood which has been concentrated and quantitatively supplies the concentrated blood into a blood vessel.

20. An extracorporeal circulation apparatus, according to claim 19, wherein:
the control of the temperature of the fluid replacement to be supplied is carried out considering heat transfer between the fluid replacement and a surrounding of the apparatus until the fluid replacement of which temperature has been adjusted is supplied into the blood vessel.

21. An extracorporeal circulation apparatus, according to claim 20, wherein:

the control of the means which controls the temperature of the fluid replacement is carried out based on Equation (II):

$$T3 = T2 - a\int_0^{l/v}(T4-Tt)t\,dt \qquad \text{Equation (II)}$$

(wherein T2 is the temperature of the supplied fluid replacement, T3 is a set temperature of the means which controls the temperature of the fluid replacement, T4 is a room temperature, l is the length of a conduit from the means which controls the temperature of the fluid replacement to the supplied fluid replacement temperature sensor, Tt is a temperature of the fluid replacement at a time t, v is a supply rate of the fluid replacement, and $a=\alpha A/V$, $\alpha$ is a heat transfer coefficient of a material of the conduit, A is a total surface area of the conduit, and V is a volume of the fluid replacement of the conduit).

22. An extracorporeal circulation apparatus, according to claim 19, wherein:
   the supplied fluid replacement is injected into the blood vessel through an artificial lung.

23. An extracorporeal circulation apparatus, according to claim 19, wherein:
   the fluid replacement supply unit supplies autologous blood or transfusion blood together with the fluid replacement, and the autologous blood or the transfusion blood is supplied through an artificial lung together with the fluid replacement into the blood vessel.

24. An extracorporeal circulation apparatus, according to claim 19, further comprising, in place of the artificial lung, a drip chamber into which oxygen is injected.

25. An extracorporeal circulation apparatus, according to claim 19, wherein:
   the fluid replacement supply unit comprises a catheter through which the fluid replacement is injected, the supplied fluid replacement temperature sensor is located at around a leading end of the catheter on a distal side thereof, the blood concentration unit comprises a catheter through which the diluted blood is withdrawn and a diluted blood temperature sensor is located at around a leading end of the catheter on a distal side thereof.

26. An extracorporeal circulation method for maintaining selective temperature control to keep an object at a predetermined temperature, which comprises the steps of:
   (A) quantitatively supplying a fluid replacement of which temperature has been adjusted into a blood vessel by means of a fluid replacement supply unit;
   (B) controlling a temperature of the fluid replacement which is quantitatively supplied by the fluid replacement supply unit based on a different extent between:
      (1) the measured diluted blood temperature and
      (2) the predetermined temperature of the object;
   (C) quantitatively withdrawing blood diluted by the fluid replacement from a blood vessel and concentrating the withdrawn blood by means of a blood concentration unit; and
   (D) measuring a temperature of the withdrawn diluted blood by means of the blood concentration unit; and
   (E) controlling a temperature of the blood which has been concentrated and quantitatively supplying the blood into a blood vessel by a blood supply unit.

27. An extracorporeal circulation method, according to claim 26, wherein controlling the temperature of the fluid replacement comprises the step of compensating for heat transfer between the fluid replacement and the atmosphere surrounding the apparatus until the temperature controlled fluid replacement is supplied into the blood vessel.

28. An extracorporeal circulation method, according to claim 26, wherein:
   upon starting the method, a temperature of the fluid replacement has been adjusted to the predetermined temperature of the object.

29. An extracorporeal circulation method, according to claim 26, wherein the method includes an extracorporeal circulation apparatus comprising:
   (A) a fluid replacement supply unit which quantitatively supplies a fluid replacement of which temperature has been adjusted into a blood vessel;
   (B) a blood concentration unit which quantitatively withdraws blood diluted by the fluid replacement from a blood vessel and concentrates the withdrawn diluted blood; and
   (C) a blood supply unit which controls a temperature of the blood and which has been concentrated and quantitatively supplies the concentrated blood into a blood vessel,
   the blood concentration unit comprising a diluted blood temperature sensor which measures a temperature of the withdrawn diluted blood, and the fluid replacement supply unit comprising a means which controls a temperature of the fluid replacement to be supplied based on a different extend between the measured diluted blood temperature and the predetermined temperature of the object.

30. An extracorporeal circulation method for maintaining selective temperature control to keep an object at a predetermined temperature, which comprises the steps of:
   (A) quantitatively supplying a fluid replacement of which temperature has been adjusted into a blood vessel by means of a fluid replacement supply unit;
   (B) controlling a temperature of the fluid replacement which is quantitatively supplied by the fluid replacement supply unit based on a different extent between the measured diluted blood temperature and the predetermined temperature of the object;
   (C) measuring a temperature of the supplied fluid replacement by means of the fluid replacement supply unit; and
   (D) controlling the temperature of the supplied fluid replacement, by means of the fluid replacement supply unit, based on a different extent between:
      (1) an averaged temperature of the measured fluid replacement temperature which is quantitatively supplied and the measured diluted blood temperature, and
      (2) the predetermined temperature of the object;
   (E) quantitatively withdrawing blood diluted by the fluid replacement from a blood vessel and concentrating the withdrawn blood by means of a blood concentration unit;
   (F) measuring a temperature of the withdrawn diluted blood by means of the blood concentration unit; and
   (G) controlling a temperature of the blood which has been concentrated and quantitatively supplying the blood into a blood vessel by a blood supply unit.

31. An extracorporeal circulation method, according to claim 30, wherein controlling the temperature of the fluid replacement comprises the step of compensating for heat transfer between the fluid replacement and the atmosphere surrounding the apparatus until the temperature controlled fluid replacement is supplied into the blood vessel.

* * * * *